United States Patent [19]

Kropp et al.

[11] Patent Number: 4,820,821

[45] Date of Patent: Apr. 11, 1989

[54] NOVEL PYRIDAZINONE-IMINES AND THEIR PHYSIOLOGICALLY TOLERATED ADDITION SALTS WITH ACIDS, THEIR PREPARATION AND THERAPEUTIC AGENTS CONTAINING THESE COMPOUNDS

[75] Inventors: Rudolf Kropp, Limburgerhof; Marco Thyes, Ludwigshafen; Rainer Schlecker, Bissersheim; Albrecht Franke, Wachenheim; Franz Reicheneder, Ludwigshafen; Dora I. Reicheneder, Ludwigshafen; August Amann, Ludwigshafen; Hans-Juergen Teschendorf, Ludwigshafen; Rolf Kretzschmar, Gruenstadt; Martin Traut, Heidelberg; Josef Gries, Wachenheim, all of Fed. Rep. of Germany

[73] Assignee: BASF Aktiengesellschaft, Ludwigshafen, Fed. Rep. of Germany

[21] Appl. No.: 39,765

[22] Filed: Apr. 17, 1987

Related U.S. Application Data

[63] Continuation of Ser. No. 438,751, Nov. 3, 1982, abandoned.

[30] Foreign Application Priority Data

Nov. 6, 1981 [DE] Fed. Rep. of Germany ....... 3144138

[51] Int. Cl.[4] .................. C07D 239/06; A61K 31/50
[52] U.S. Cl. .................................................. 544/224
[58] Field of Search ........................ 514/247; 544/224

[56] References Cited

U.S. PATENT DOCUMENTS

| | | | |
|---|---|---|---|
| 3,631,038 | 12/1971 | Reicheneder et al. | 544/114 |
| 3,980,633 | 9/1976 | Kropp et al. | 544/224 |
| 4,011,220 | 3/1977 | Kropp et al. | 544/224 |
| 4,648,896 | 3/1987 | Brunner et al. | 71/92 |

FOREIGN PATENT DOCUMENTS

| | | |
|---|---|---|
| 645360 | 3/1963 | Belgium . |
| 1542693 | 8/1965 | Fed. Rep. of Germany . |
| 1770772 | 7/1968 | Fed. Rep. of Germany . |
| 1912941 | 3/1969 | Fed. Rep. of Germany . |
| 2139687 | 8/1971 | Fed. Rep. of Germany . |
| 2211662 | 3/1972 | Fed. Rep. of Germany . |
| 2245248 | 9/1972 | Fed. Rep. of Germany . |
| 1406061 | 9/1975 | United Kingdom . |

OTHER PUBLICATIONS

"Mode of Action of Herbicides", by F. M. Ashton & A. S. Crafts, Wiley–Interscience Publication, (New York), (1973).

Martin-Escvdero Perez et al., Chemical Abstracts, vol. 103, 123499x, (1985).

Goday et al., Chemical Abstracts, vol. 106, 84626b, (1987).

Primary Examiner—Donald G. Daus
Assistant Examiner—E. Bernhardt
Attorney, Agent, or Firm—Keil & Weinkauf

[57] ABSTRACT

Novel 1-phenyl-4(1H)-pyridazinone-imines of the formula (I)

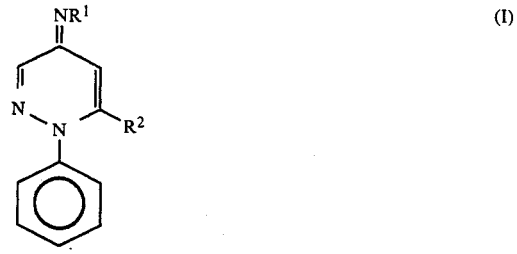

which are substituted at the imine nitrogen, and their addition salts with a physiologically tolerated acid, processes for their preparation, pharmaceutical formulations containing these compounds, and their use as drugs, in particular as antidepressants, antiparkinson drugs and antihypotonic agents.

6 Claims, No Drawings

NOVEL PYRIDAZINONE-IMINES AND THEIR PHYSIOLOGICALLY TOLERATED ADDITION SALTS WITH ACIDS, THEIR PREPARATION AND THERAPEUTIC AGENTS CONTAINING THESE COMPOUNDS

This application is a continuation of application Ser. No. 438,751, filed on Nov. 3, 1982 now abandoned.

The present invention relates to novel 1-phenyl-4(1H)-pyridazinone-imines of the formula (I)

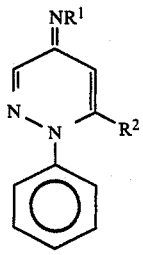
(I)

which are substituted at the imine nitrogen, and their addition salts with a physiologically tolerated acid, processes for their preparation, pharmaceutical formulations containing these compounds, and their use as drugs, in particular antidepressants, antiparkinson drugs and antihypotonic agents.

It should be pointed out that the addition salts of the compounds of the formula (I) with acids can also be formulated as pyridazinium salts of the formula (II)

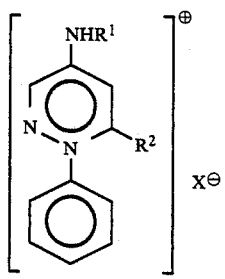
(II)

where $X^\ominus$ is the acid anion.

A number of 4(1H)-pyridazinone-imines having various substituents have been described, for example in Belgian Pat. No. 645,360 and German laid-open application DOS Nos. 1,542,693 and DOS 1,770,772, and these compounds are said to be used as intermediates for the preparation of dyes, insecticides, crop protection agents or herbicides. German laid-open application DOS Nos. 1,912,941, DOS 2,139,687, DOS 2,211,662 and DOS 2,245,248 describe pyridazinium salts which have an amine radical in the 4-position; these salts are said to be used as intermediates for the preparation of dyes, drugs and pesticides, and some of them are described as drugs with an antidepressive and hypertensive action.

The specially substituted compounds to which the present invention relates have not been prepared to date.

We have found that 1-phenyl-4(1H)-pyridazinoneimines of the formula (I)

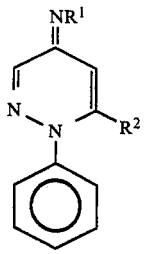
(I)

where $R^1$ is an acyl radical $-CO-R^3$ where $R^3$ is alkyl of 1 to 8 carbon atoms or benzyl which can be monosubstituted, disubstituted or trisubstituted in the phenyl ring by identical or different substituents from the group comprising alkyl of 1 to 3 carbon atoms, alkoxy where alkyl is of 1 to 3 carbon atoms, halogen and trifluoromethyl, or is cycloalkyl of 3 to 8 ring carbon atoms which is unsubstituted or monosubstituted, disubstituted, trisubstituted or tetrasubstituted by alkyl of 1 to 4 carbon atoms, or is alkenyl of 2 to 8 carbon atoms, or phenyl which is unsubstituted or monosubstituted, disubstituted or trisubstituted by identical or different substituents from the group comprising alkyl of 1 to 4 carbon atoms, alkoxy where alkyl is of 1 to 4 carbon atoms, halogen and trifluoromethyl, or $R^1$ is $-CO-Y-R^4$, where Y is oxygen or sulfur, and $R^4$ is alkyl of 1 to 8 carbon atoms, or benzyl which can be monosubstituted, disubstituted or trisubstituted in the phenyl ring by identical or different substituents from the group comprising alkyl of 1 to 3 carbon atoms, alkoxy where alkyl is of 1 to 3 carbon atoms, halogen and trifluoromethyl, or is alkenyl which is of 3 to 8 carbon atoms and in which the double bond is separated from Y by an alkylene chain of one or more carbon atoms, or is phenyl which is unsubstituted or monosubstituted, disubstituted or trisubstituted by identical or different substituents from the group comprising alkyl of 1 to 4 carbon atoms, alkoxy where alkyl is of 1 to 4 carbon atoms, halogen and trifluoromethyl, or $R^1$ is

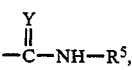

where Y is oxygen or sulfur, and $R^5$ is alkyl of 1 to 8 carbon atoms, or benzyl which can be monosubstituted, disubstituted or trisubstituted in the phenyl ring by identical or different substituents from the group comprising alkyl of 1 to 3 carbon atoms, alkoxy where alkyl is of 1 to 3 carbon atoms, halogen and trifluoromethyl, or is phenyl which is unsubstituted or monosubstituted, disubstituted or trisubstituted by identical or different substituents from the group comprising alkyl of 1 to 4 carbon atoms, alkoxy where alkyl is of 1 to 4 carbon atoms, halogen and trifluoromethyl, or $R^1$ is $-CO-COO-R^6$, where $R^6$ is alkyl of 1 to 8 carbon atoms, and $R^2$ is hydrogen or alkoxy where alkyl is of 1 to 8 carbon atoms, and their addition salts with a physiologically tolerated inorganic or organic hydroacid, possess useful pharmacological properties.

$R^3$ in $-CO-R^3$, $R^4$ in $-CO-Y-R^4$, $R^5$ in

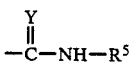

and $R^6$ in $-CO-COO-R^6$, where $R^3$, $R^4$, $R^5$ and $R^6$ are each alkyl of 1 to 8 carbon atoms, are, for example, straightchain or branched alkyl radicals, such as methyl, ethyl, propyl, isopropyl, butyl, isobutyl, sec.-butyl, tert.-butyl, pentyl, 1-methylbutyl, 2-methylbutyl, isopentyl, 1,1-dimethylpropyl, 2,2-dimethylpropyl, hexyl, heptyl or octyl.

$R^3$ in $-CO-R^3$, $R^4$ in $-CO-Y-R^4$ and $R^5$ in

where $R^3$, $R^4$ and $R^5$ are each benzyl which is monosubstituted, disubstituted or trisubstituted in the phenyl ring by identical or different substituents from the group comprising alkyl of 1 to 3 carbon atoms, eg. methyl, ethyl or propyl, alkoxy where alkyl is of 1 to 3 carbon atoms, eg. methoxy or ethoxy, halogen, eg. chlorine, bromine or fluorine, and trifluoromethyl, are, for example, 2-methylbenzyl, 3-methylbenzyl, 4-methylbenzyl, 4-ethylbenzyl, 2,4-dimethylbenzyl, 2,5-dimethylbenzyl, 3,4-dimethylbenzyl, 3,5-dimethylbenzyl, 2-methoxybenzyl, 3-methoxybenzyl, 4-methoxybenzyl, 4-ethoxybenzyl, 2,3-dimethoxybenzyl, 2,4-dimethoxybenzyl, 2,5-dimethoxybenzyl, 3,4-dimethoxybenzyl, 3,5-dimethoxybenzyl, 3,4,5-trimethoxybenzyl, 2-chlorobenzyl, 3-chlorobenzyl, 4-chlorobenzyl, 2,4-dichlorobenzyl, 2,5-dichlorobenzyl, 2,6-dichlorobenzyl, 3,4-dichlorobenzyl, 3,5-dichlorobenzyl, 2-bromobenzyl, 3-bromobenzyl, 4-bromobenzyl, 2-fluorobenzyl, 3-fluorobenzyl, 4-fluorobenzyl, 2-chloro-4-fluorobenzyl, 2-chloro-6-fluorobenzyl, 4-chloro-2-fluorobenzyl, 5-chloro-2-fluorobenzyl, 2-(trifluoromethyl)-benzyl, 3-(trifluoromethyl)-benzyl and 4-(trifluoromethyl)-benzyl.

$R^3$ in $-CO-R^3$, where $R^3$ is cycloalkyl of 3 to 8 ring carbon atoms which is unsubstituted or monosubstituted, disubstituted, trisubstituted or tetrasubstituted by alkyl of 1 to 4 carbon atoms, is, for example, cyclopropyl, 1-methylcyclopropyl, 2-methylcyclopropyl, 2,2-dimethylcyclopropyl, 1,2,2-trimethylcyclopropyl, 2,2,3-trimethylcyclopropyl, 2,2,3,3-tetramethylcyclopropyl, 1-butylcyclopropyl, cyclobutyl, 1-methylcyclobutyl, 2-methylcyclobutyl, 3-methylcyclobutyl, 3,3-dimethylcyclobutyl, 1-propylcyclobutyl, 1-butylcyclobutyl, 3-tert.-butylcyclobutyl, cyclopentyl, 1-methylcyclopentyl, 2,5-dimethylcyclopentyl, cyclohexyl, 1-methylcyclohexyl, 2-ethylcyclohexyl, cycloheptyl and cyclooctyl.

$R^3$ in $-CO-R^3$, where $R^3$ is alkenyl of 2 to 8 carbon atoms, is, for example, vinyl, prop-1-enyl, isopropenyl, allyl, 1-methylprop-1-enyl, 2-methylprop-1-enyl, 1-methylprop-2-enyl, but-1-enyl, but-2-enyl, but-3-enyl, 1,2-dimethylprop-1-enyl, 1-ethylprop-1-enyl, 2-methylbut-1-enyl, 3-methylbut-1-enyl, 1-methylbut-2-enyl, 2-methylbut-2-enyl, pent-1-enyl, pent-2-enyl, pent-3-enyl, pent-4-enyl, 1-ethylbut-1-enyl, 2-ethylbut-1-enyl, 1,3-dimethylbut-1-enyl, 2-methylpent-1-enyl, 3-methylpent-1-enyl, 3-methylpent-2-enyl, 4-methylpent-3-enyl, hex-3-enyl, hex-5-enyl, 2-ethyl-1-methylbut-1-enyl, 1,4-dimethylpent-3-enyl, hept-1-enyl, hept-6-enyl, oct-1-enyl and oct-7-enyl.

$R^4$ in $-CO-Y-R^4$, where $R^4$ is alkenyl of 3 to 8 carbon atoms and the double bond is separated from Y by an alkylene chain of one or more carbon atoms, is, for example, allyl, but-2-enyl, but-3-enyl, 1-methylallyl, 2-methylallyl, 1,1-dimethylallyl, 1-ethylallyl, 1-methylbut-2-enyl, 3-methylbut-2-enyl, 1-methylbut-3-enyl, 3-methylbut-3-enyl, pent-4-enyl, 1-propylallyl, hex-2-enyl, hex-3-enyl, 1,5-dimethylhex-4-enyl and 1-pentylallyl.

$R^3$ in $-CO-R^3$, $R^4$ in $-CO-Y-R^4$ and $R^5$ in

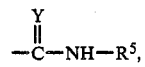

where $R^3$, $R^4$ and $R^5$ are each phenyl which is monosubstituted, disubstituted or trisubstituted by identical or different substituents from the group comprising alkyl of 1 to 4 carbon atoms, eg. methyl, ethyl or propyl, alkoxy where alkyl is of 1 to 4 carbon atoms, eg. methoxy or ethoxy, halogen, eg. chlorine, bromine or fluorine, and trifluoromethyl, are, for example 2-tolyl, 3-tolyl, 4-tolyl, 2-ethylphenyl, 3-ethylphenyl, 4-ethylphenyl, 2-propylphenyl, 4-propylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 2,3,5-trimethylphenyl, 2,3,6-trimethylphenyl, 2-methoxyphenyl, 3-methoxyphenyl, 4-methoxyphenyl, 2-ethoxyphenyl, 4-ethoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,4,5-trimethoxyphenyl, 2,4,6-trimethoxyphenyl, 3,4,5-trimethoxyphenyl, 2-chlorophenyl, 3-chlorophenyl, 4-chlorophenyl, 2-bromophenyl, 3-bromophenyl, 4-bromophenyl, 2-fluorophenyl, 3-fluorophenyl, 4-fluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4-difluorophenyl, 2,5-difluorophenyl, 2,6-difluorophenyl, 2-chloro-6-fluorophenyl, 3-chloro-4-fluorophenyl, 2-(trifluoromethyl)-phenyl, 3-(trifluoromethyl)-phenyl, 4-(trifluoromethyl)-phenyl, 2-methoxy-5-methylphenyl, 3-methoxy-4-methylphenyl, 4-methoxy-2-methylphenyl, 4-methoxy-3-methylphenyl, 2-ethoxy-4-ethylphenyl, 2-chloro-4-methylphenyl, 2-chloro-5-methylphenyl, 2-chloro-6-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2-chloro-5-methoxyphenyl, 3-chloro-4-methoxyphenyl, 3-chloro-5-methoxyphenyl, 4-chloro-2-methoxyphenyl, 5-chloro-2-methoxyphenyl, 4-chloro-2,5-dimethoxyphenyl, 5-chloro-2,4-dimethyloxyphenyl, 3-fluoro-4-methylphenyl, 5-fluoro-2-methylphenyl, 3-fluoro-4-methoxyphenyl, 5-methoxy-3-(trifluoromethyl)-phenyl, 2-chloro-5-(trifluoromethyl)-phenyl, 4-chloro-2-(trifluoromethyl)-phenyl, 4-chloro-3-(trifluoromethyl)-phenyl, 4-fluoro-2-(trifluoromethyl)-phenyl and 4-fluoro-3-(trifluoromethyl)-phenyl.

Alkoxy radicals $R^2$ where alkyl is of 1 to 8 carbon atoms are, for example, methoxy, ethoxy, propoxy, isopropoxy, butoxy, sec.-butoxy, isobutoxy, tert.-butoxy, pentyloxy, 1-methylbutoxy, 2-methylbutoxy, isopentyloxy, 1,1-dimethylpropoxy, 2,2-dimethylpropoxy, hexyloxy, heptyloxy and octyloxy.

Preferred compounds of the formula (I), where the substituents have meanings mentioned above, are those in which $R^1$ is an acyl radical $-CO-R^3$ where $R^3$ is alkyl of 1 to 8 carbon atoms, or benzyl which can be monosubstituted in the phenyl ring by fluorine, chlorine or methoxy, or is cycloalkyl of 3 to 6 ring carbon atoms which is unsubstituted or monosubstituted or disubstitutted by methyl, or is alkenyl of 2 to 4 carbon atoms, or phenyl which is unsubstituted or monosubstituted or disubstituted by a substituent from the group comprising alkyl of 1 to 3 carbon atoms, alkoxy where alkyl is of 1 to 3 carbon atoms, halogen and trifluoromethyl, or $R^1$ is —CO—Y—$R^4$ where Y is oxygen or sulfur, and $R^4$ is alkyl of 1 to 4 carbon atoms or benzyl which can be monosubstituted in the phenyl ring by fluorine, chlorine or methoxy, or is alkenyl which is of 3 to 6 carbon atoms and in which the double bond is separated from Y by an alkylene chain of one or more carbon atoms, or is phenyl which is unsubstituted or monosubstituted or disubstituted by a substituent from the group comprising alkyl of 1 to 3 carbon atoms, alkoxy where alkyl is of 1 to 3 carbon atoms, halogen and trifluoromethyl, or $R^1$ is

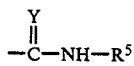

where Y is oxygen or sulfur, and $R^5$ is alkyl of 1 to 6 carbon atoms, or benzyl which can be monosubstituted in the phenyl ring by fluorine, chlorine or methoxy, or is phenyl which is unsubstituted or monosubstituted or disubstituted by a substituent from the group comprising alkyl of 1 to 3 carbon atoms, alkoxy where alkyl is of 1 to 3 carbon atoms, halogen and trifluoromethyl, or $R^1$ is —CO—COO—$R^6$ where $R^6$ is alkyl of 1 to 4 carbon atoms, and $R^2$ is hydrogen or alkoxy where alkyl is of 1 to 4 carbon atoms, and their addition salts with a physiologically tolerated acid.

Suitable acids are the conventional physiologically tolerated inorganic and organic hydracids, eg. hydrochloric acid, hydrobromic acid, phosphoric acid, sulfuric acid, methylsulfuric acid, ethylsulfuric acid, oxalic acid, maleic acid, fumaric acid, lactic acid, tartaric acid, malic acid, citric acid, salicylic acid, adipic acid and benzoic acid.

Conventionally used physiologically tolerated acids are also mentioned in Fortschritte der Arzneimittelforschung, Volume 10, pages 224 and 225, Birkhäuser Verlag, Basel and Stuttgart, 1996, and J. Pharm. Sci., 66 (1977), 1–5.

The novel pyridazinone-imines of the formula (I) where $R^1$ is an acyl group —CO—$R^3$, and their addition salts with a physiologically tolerated acid, can be prepared by a process wherein a compound of the formula (III)

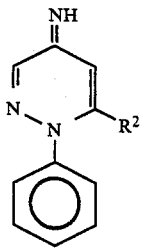

where $R^2$ has the meanings given for formula (I), if appropriate in the form of any desired addition salt with an acid, is reacted in a conventional manner with an acylating agent of the formula (IV)

where $R^3$ has the meanings given for the acyl radical —CO—$R^3$ in formula (I), and A is halogen, in particular chlorine, or —O—CO—$R^3$ where $R^3$ has the meanings given for formula (IV), and if the compound obtained is the free imine, this may, if required, be converted in a conventional manner into an addition salt with a physiologically tolerated acid, or if an addition salt with an acid is obtained, this may, if required, be converted in a conventional manner into an addition salt with another, physiologically tolerated acid, or into the free imine.

Conversion of an addition salt obtained in the preparation process is particularly appropriate when the starting compound of the formula (III) which is employed is in the form of an addition salt with an acid which can be regarded only with qualification as being physiologically tolerated.

In accordance with the meanings given for A, advantageous acylating agents are the corresponding carboxylic acid halides, in particular chlorides, and the corresponding carboxylic acid anhydrides.

The acylation of a free compound of the formula (III) with an acylating agent of the formula (IV) is carried out under conventional conditions, as a rule using an equimolar amount or an excess of the acylating agent, advantageously in the presence of a solvent or diluent, if appropriate in a two-phase system comprising water and a water-immiscible solvent, in the presence or absence of a base as an acid acceptor, and under atmospheric or superatmospheric pressure.

Compounds of the formula (III) where $R^2$ is alkoxy are advantageously reacted at from 0° to 50° C., and those where $R^2$ is hydrogen are reacted at from 0° to 120° C., preferably at 0° to 80° C. The reaction may be carried out at the boiling point of the reaction mixture where this boiling point falls within the temperature range given.

Suitable solvents or diluents are those which are inert under the reaction conditions, for example aromatic hydrocarbons, eg. toluene or xylene, aliphatic or aromatic chlorohydrocarbons, eg. methylene chloride, ethylene chloride or chlorobenzene, open-chain or cyclic aliphatic ethers, eg. diethyl ether, tetrahydrofuran or dioxane, dialkyl ketone, eg. acetone or diethyl ketone, or dialkylformamides, eg. dimethylformamide. If appropriate, a liquid acylating agent (IV) may be used in excess as the solvent or diluent. It is also possible to use water or a mixture of water with a water-miscible solvent which is inert under the reaction conditions, eg. acetone. In this case, however, the acylating agent employed must not be readily hydrolyzable.

When the acylation is carried out in a two-phase system, suitable water-immiscible solvents which are inert under the reaction conditions are, for example, aromatic hydrocarbons, such as toluene and xylene, aliphatic or aromatic chlorohydrocarbons, such as methylene chloride, ethylene chloride and chlorobenzene, and aliphatic ethers, such as diethyl ether. If the reaction is carried out in a two-phase system using a readily hydrolyzable acylating agent, it is advantageous initially to introduce the compound of the formula (III), and if a base is used, initially to introduce this as well or to add it simultaneously with the acylating agent.

Advantageously, the bases used as acid acceptors are inorganic bases, eg. sodium hydroxide, potassium hydroxide, sodium carbonate, potassium carbonate, sodium bicarbonate or potassium bicarbonate, or tertiary organic amines, in particular triethylamine.

The acylation of a compound of the formula (III) with a carboxylic acid anhydride can be carried out in the presence of a mineral acid, eg. sulfuric acid or perchloric acid, as a catalyst.

The free compounds of the formula (III) where $R^2$ is alkoxy can be obtained from their addition salts with acids in a conventional manner, for example by treating a solution or suspension of the salt in water with a base, eg. sodium hydroxide, at from 0° to 30° C., preferably from 0° to 15° C., and can be isolated by a conventional method, at from 0° to 30° C., preferably from 0° to 15° C. However, it is more advantageous not to isolate the free compound (III) but instead to use the addition salt with an acid, this salt being converted in a conventional manner, in the reaction medium, with a base, eg. sodium hydroxide, potassium hydroxide, sodium carbonate, potassium carbonate, sodium bicarbonate, potassium bicarbonate or triethylamine, to give the free compound, which is then reacted.

The 1,4-dihydro-4-imino-1-phenylpyridazine (III, $R^2=H$) to be acylated may also be used in the form of the free base or of an addition salt, with an acid, which is converted, in the reaction medium, with a base, eg. sodium hydroxide, potassium hydroxide, sodium carbonate, potassium carbonate, sodium bicarbonate, potassium bicarbonate or triethylamine, to give the free compound.

An addition salt of a compound of the formula (III) with an acid is acylated directly with an acylating agent of the formula (IV) likewise under conventional conditions, as a rule using an equimolar amount or an excess of the acylating agent, advantageously in the presence of a solvent or diluent, at from 20° to 180° C., if appropriate at the boiling point of the reaction mixture, and under atmospheric or superatmospheric pressure.

Suitable solvents or diluents are those which are inert under the reaction conditions, for example aromatic hydrocarbons, eg. toluene or xylene, aliphatic or aromatic hydrocarbons, eg. ethylene chloride or chlorobenzene, open-chain or cyclic aliphatic ethers, eg. dibutyl ether or dioxane, ketones, eg. diethyl ketone, or dialkylformamides, eg. dimethylformamide. If appropriate, the acid from which the acylating agent is derived may be used as the solvent or diluent. Where a liquid acylating agent (IV) is employed, this may, if appropriate, be used in excess as the solvent or diluent.

Where a carboxylic acid anhydride is used as the acylating agent, the reaction can be carried out in the presence of a mineral acid, eg. sulfuric acid or perchloric acid, as a catalyst.

The novel pyridazinone-imines of the formula (I) where $R^1$ is $-CO-Y-R^4$, and their addition salts with a physiologically tolerated acid, can be prepared by a process wherein a compound of the formula (III) where $R^2$ has the meanings given for formula (I), if appropriate in the form of any desired addition salt with an acid, is reacted in a conventional manner with a compound of the formula (V)

$$R^4-Y-CO-B \qquad (V)$$

where $R^4$ and Y have the meanings given for the radical $-CO-Y-R^4$ in formula (I), and B is halogen, in particular chlorine, and when the compound obtained is the free imine, this may, if appropriate, be converted in a conventional manner into an addition salt with a physiologically tolerated acid, or if an addition salt with an acid is obtained, this may, if appropriate, be converted in a conventional manner into an addition salt with another, physiologically tolerated acid, or into the free imine.

The reaction of a compound of the formula (III), or of one of its addition salts with an acid, with a haloformate or haloformic acid S-ester (V), is carried out under the conditions given above for the acylation of a compound of the formula (III), or of one of its addition salts with an acid, with a carboxylic acid halide of the formula (IV) (A=halogen).

The novel pyridazinone-imines of the formula (I) where $R^1$ is

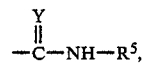

and their addition salts with a physiologically tolerated acid, can be prepared by a process wherein a compound of the formula (III) where $R^2$ has the meanings given for formula (I), if appropriate in the form of any desired addition salt with an acid, is reacted in a conventional manner with a compound of the formula (VI)

$$R^5-N=C=Y \qquad (VI)$$

where $R^5$ and Y have the meanings given for

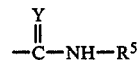

in formula (I), and where the resulting compound is the free imine, this may, if required, be converted in a conventional manner into an addition salt with a physiologically tolerated acid, or if an addition salt with an acid is obtained, this may, if required, be converted in a known manner into an addition salt with another, physiologically tolerated acid, or into the free imine.

The reaction of a compound of the formula (III), or of one of its addition salts with an acid, with an isocyanate or isothiocyanate (VI) is carried out under the conditions given above for the acylation of a compound of the formula (III), or of its addition salt with an acid, with a carboxylic acid halide of the formula (IV) (A=halogen). However, a base is of course not used in the reaction of a compound of the formula (III) with an isocyanate or isothiocyanate.

To prepare the compounds (I) in which $R^1$ is

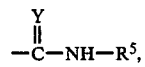

and their addition salts with a physiologically tolerated acid, the isocyanate or isothiocyanate (VI) is preferably allowed to react with a free compound, and the free imine obtained may if required be converted into an addition salt with a physiologically tolerated acid. In carrying out the reaction with a compound (VI), a catalyst conventionally employed to accelerate isocyanate reactions, eg. triethylamine, may be added.

The novel pyridazinone-imines of the formula (I) where $R^1$ is $-CO-COO-R^6$, and their addition salts with a physiologically tolerated acid, can be prepared by a process in which a compound of the formula (III) where $R^2$ has the meanings given for formula (I), if appropriate in the form of any desired addition salt with an acid, is reacted in a conventional manner with an oxalic acid ester chloride of the formula (VII)

$$R^6\text{—OOC—CO—Cl} \qquad (VII)$$

where $R^6$ has the meanings given for the radical —CO—COO—$R^6$ in formula (I), and if the free imine is obtained, this may, if appropriate, be converted in a conventional manner into an addition salt with a physiologically tolerated acid, or if an addition salt with an acid is obtained, this may, if required, be converted in a conventional manner into an addition salt with another, physiologically tolerated acid, or into the free imine.

A compound of the formula (III), or one of its addition salts with an acid, is reacted with an oxalic acid ester chloride (VII) under the conditions given above for the acylation of a compound of the formula (III), or of one of its addition salts with an acid, with a carboxylic acid halide of the formula (IV) (A=halogen).

The conversion of a novel compound obtained as the free imine into an addition salt with a physiologically tolerated acid is carried out, as stated above, by a conventional method, as a rule by reacting the free base with the appropriate physiologically tolerated acid. The reaction can be carried out, for example, by mixing the base with the acid in water, in an organic solvent, for example a lower alcohol, eg. methanol or ethanol, a ketone, eg. acetone or diethyl ketone, a chlorohydrocarbon, eg. methylene chloride or ethylene chloride, or an ether, eg. diethyl ether, tetrahydrofuran or dioxane, in a mixture of the above organic solvents, in a mixture of water with one of the above water-miscible organic solvents, or in a two-phase system comprising water and one of the above water-immiscible organic solvents. It is also possible, for example, to mix a solution of the free base in one of the above organic solvents with a solution of the acid in water or in one of the above organic solvents.

The novel compound obtained as an addition salt with an acid can, as stated above, be converted in a conventional manner, for example with a base or an ion exchanger, into the free compound.

As stated above, a conventional process may likewise be employed when an addition salt of a compound of the formula (I) with an acid is converted into an addition salt with another, physiologically tolerated acid. For example, the initially obtained salt may be converted into the free compound and the latter converted into the desired addition salt with an acid, or the anion of the initially obtained salt may be exchanged for the anion of another, physiologically tolerated acid by means of an ion exchanger.

The addition salts of the pyridazinone-imines of the formula (III), which salts are used as starting compounds, are disclosed in German Laid-Open Applications DOS 1,912,941 and DOS 2,245,248, or may be prepared by the methods described therein. 1,4-Dihydro-4-imino-1-phenylpyridazine, which is used as a starting material, can be prepared from one of its addition salts with an acid, which are described in German Laid-Open Application DOS 2,245,248, by treating the salt in water with sodium hydroxide. The compound is crystalline, and melts at 97°–98° C. (recrystallization from cyclohexane).

Examples of novel compounds which are obtained by the above processes are 4-acetylimino-1,4-dihydro-1-phenylpyridazine; 6-methoxy-, 6-ethoxy-, 6-propoxy-, 6-isopropoxy-, 6-butoxy-, 6-(sec.-butoxy)-, 6-isobutoxy-, 6-(tert.-butoxy)-, 6-pentyloxy,-, 6-hexyloxy-, 6-heptyloxy- and 6-octyloxy-4-acetylimino-1,4-dihydro-1-phenylpyridazine; 1,4-dihydro-1-phenyl-4-(propionylimino)-pyridazine; 6-methoxy-, 6-ethoxy-, 6-propoxy-, 6-isopropoxy-, 6-butoxy-, 6-(sec.-butoxy)-, 6-isobutoxy-, 6-pentyloxy-, 6-hexyloxy-, 6-heptyloxy- and 6-octyloxy-1,4-dihydro-1-phenyl-4-(propionylimino)-pyridazine; 4,4-butyrylimino-1,4-dihydro-1-phenylpyridazine; 6-methoxy-, 6-ethoxy-, 6-propoxy-, 6-isopropoxy-, 6-butoxy-, 6-(sec.-butoxy)-, 6-isobutoxy-, 6-pentyloxy- and 6-octyloxy-4-butyrylimino-1,4-dihydro-1-phenylpyridazine; 1,4-dihydro-4-isobutyrylimino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-isobutyrylimino-1-phenylpyridazine; 1,4-dihydro-1-phenyl-4-(valerylimino)-pyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-1-phenyl-4-(valerylimino)-pyridazine; 1,4-dihydro-4-(2-methylbutyryl)-imino-1-phneylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-(2-methylbutyryl)-imino-1-phenylpyridazine; 1,4-dihydro-4-isovaleryl-imino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-isovalerylimino-1-phenylpyridazine; 1,4-dihydro-1-phenyl-4-(pivaloylimino)pyridazine; 6-methoxy-, 6-ethoxy-, 6-propoxy- 6-isopropoxy-, 6-butoxy, 6-isobutoxy-, 6-pentyloxy- and 6-octyloxy-1,4-dihydro-1-phenyl-4-(pivaloylimino)-pyridazine; 1,4-dihydro-4-hexanoylimino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-hexanoylimino-1-phenylpyridazine; 1,4-dihydro-4-heptanoylimino-1-phenylpyridazine; 6-methoxy-, 6-ethoxy-, 6-propoxy-, 6-isopropoxy-, 6-butoxy-, 6-isobutoxy-, 6-pentyloxy-, and 6-octyloxy-1,4-dihydro-4-heptanoylimino-1-phenylpyridazine; 1,4-dihydro-4-octanoylimino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-octanoylimino-1-phenylpyridazine; 1,4-dihydro-4-nonanoylimino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-nonanoylimino-1-phenylpyridazine; 1,4-dihydro-1-phenyl-4-[(phenylacetyl)-imino]-pyridazine; 6-methoxy-, 6-ethoxy-, 6-propoxy-, 6-isopropoxy-, 6-butoxy-, 6-(sec.-butoxy)-, 6-isobutoxy-, 6-pentyloxy-, 6-hexyloxy- and 6-octyloxy-1,4-dihydro-1-phenyl-4-[(phenylacetyl)-imino]-pyridazine; 1,4-dihydro-1-phenyl-4-[(o-tolylacetyl)-imino]-pyridazine; 6-methoxy-, 6-ethoxy-, 6-propoxy-, 6-isopropoxy-, 6-butoxy- and 6-pentyloxy-1,4-dihydro-1-phenyl-4-[(o-tolylacetyl)-imino]-pyridazine; 1,4-dihydro-1-phenyl-4-[(m-tolylacetyl)-imino]-pyridazine; 6-methoxy-, 6-ethoxy-, 6-propoxy-, 6-isopropoxy, 6-butoxy- and 6-pentyloxy-1,4-dihydro-1-phenyl-4-[(m-tolylacetyl)-imino]-pyridazine; 1,4-dihydro-1-phenyl-4-[(p-tolylacetyl)-imino]-pyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-1-phenyl-4-[(p-tolylacetyl)-imino]-pyridazine; 1,4-dihydro-4-(o,p-dimethylphenylacetyl)-imino-1-phenylpyridazine; 6-methoxy-, 6-ethoxy-, 6-propoxy-, 6-isopropoxy- and 6-butoxy-1,4-dihydro-4-(o,p-dimethylphenylacetyl)-imino-1-phenylpyridazine; 1,4-dihydro-4-(o-methoxyphenylacetyl)-imino-1-phenylpyridazine; 6-methoxy-, 6-ethoxy-, 6-propoxy-, 6-isopropoxy-, 6- butoxy- and 6-isobutoxy-1,4-dihydro-4-(o-methoxyphenylacetyl)-imino-1-phenylpyridazine; 1,4-dihydro-4-(m-methoxyphenylacetyl)-imino-1-phenylpyridazine; 6-methoxy-, 6-ethoxy-, 6-propoxy-, 6-isopropoxy-, 6-butoxy- and 6-isobutoxy-1,4-dihydro-4-(m-methoxyphenylacetyl)-imino-1-phenylpyridazine; 1,4-dihydro-4-(p-methoxyphenylacetyl)-imino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-(p-methoxyphenylacetyl)-imino-1-phenylpyridazine; 1,4-dihydro-4-[(2,5-dimethoxyphenylacetyl]-imino-1-phenylpyridazine; 6-methoxy-, 6-ethoxy-, 6-propoxy-, 6-isopropoxy-, 6-butoxy- and 6-isobutoxy-1,4-dihydro-4-[(2,5-dimethoxyphenyl)-acetyl]-imino-1-phenylpyridazine; 1,4-dihydro-4-[(3,4-dimethoxyphenyl)-acetyl]-imino-1-phenylpyridazine; 6-methoxy-, 6-ethoxy-, 6-propoxy-, 6-isopropoxy-, 6-butoxy-, 6-isobutoxy- and 6-pentyloxy-1,4-dihydro-4-[(3,4-dimethoxyphenyl)-acetyl]-imino-1-phenylpyridazine; 1,4-dihydro-1-phenyl-4-[(m,m′,p-trimethoxyphenylacetyl)-imino]-pyridazine; 6-methoxy-, 6-ethoxy-, 6-propoxy- and 6-butoxy-1,4-dihydro-1-phenyl-4-[(m,m′,p-trimethoxyphenylacetyl)-imino]-pyridazine; 4-(o-chlorophenylacetyl)-imino-1,4-dihydro-1-phenylpyridazine; 6-methoxy-, 6-ethoxy-, 6-propoxy-, 6-isopropoxy-, 6-butoxy- and 6-isobutoxy-4-(o-chlorophenylacetyl)-imino-1,4-dihydro-1-phenylpyridazine; 4-(m-chlorophenylacetyl)-imino-1,4-dihydro-1-phenylpyridazine; 6-methoxy-, 6-ethoxy-, 6-propoxy-, 6-isopropoxy-, 6-butoxy-, 6-isobutoxy- and 6-pentyloxy-4-(m-chlorophenylacetyl)-imino-1,4-dihydro-1-phenylpyridazine; 4-(p-chlorophenylacetyl)-imino-1,4-dihydro-hydro-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-4-(p-chlorophenylacetyl)-imino-1,4-dihydro-1-phenylpyridazine; 4-(o,p-dichlorophenylacetyl)-imino-1,4-dihydro-1-phenylpyridazine; 6-methoxy-, 6-ethoxy-, 6-propoxy-, 6-isopropoxy-, 6-butoxy- and 6-pentyloxy-4-(o,p-dichlorophenylacetyl)-imino-1,4-dihydro-1-phenylpyridazine; 4-(m,p-dichlorophenylacetyl)-imino-1,4-dihydro-1-phenylpyridazine; 6-methoxy-, 6-ethoxy-, 6-propoxy-, 6-isopropoxy-, 6-butoxy- and 6-pentyloxy-4-(m,p-dichlorophenylacetyl)-imino-1,4-dihydro-1-phenylpyridazine; 1,4-dihydro-4-(o-fluorophenylacetyl)-imino-1-phenylpyridazine; 6-methoxy-, 6-ethoxy-, 6-propoxy-, 6-isopropoxy-, 6-butoxy-, 6-isobutoxy- and 6-pentyloxy-1,4-dihydro-4-(o-fluorophenylacetyl)-imino-1-phenylpyridazine; 1,4-dihydro-4-(p-fluorophenylacetyl)-imino-1-phenylpyridazine; 6-methoxy-, 6-ethoxy-, 6-propoxy-, 6-isopropoxy-, 6-butoxy-, 6-isobutoxy-, 6-pentyloxy- and 6-octyloxy-1,4-dihydro-4-(p-fluorophenylacetyl)-imino-1-phenylpyridazine; 4-(o-chloro-o-fluorophenylacetyl)-imino-1,4-dihydro-1-phenylpyridazine; 6-methoxy-, 6-ethoxy-, 6-propoxy- and 6-butoxy-4-(o-chloro-o-fluorophenylacetyl)-imino-1,4-dihydro-1-phenylpyridazine; 1,4-dihydro-1-phenyl-4-{[m-(trifluoromethyl)-phenylacetyl]-imino}-pyridazine; 6-methoxy-, 6-ethoxy-, 6-propoxy-, 6-isopropoxy-, 6-butoxy-, 6-isobutoxy- and 6-pentyloxy-1,4-dihydro-1-phenyl-4-{[m-(trifluoromethyl)-phenylacetyl]-imino}-pyridazine; 4-(cyclopropylcarbonyl)-imino-1,4-dihydro-1-phenylpyridazine; 6-methoxy-, 6-ethoxy-, 6-propoxy-, 6-isopropoxy-, 6-butoxy-, 6-(sec.-butoxy)-, 6-isobutoxy-, 6-pentyloxy- and 6-octyloxy-4-(cyclopropylcarbonyl)-imino-1,4-dihydro-1-phenylpyridazine; 1,4-dihydro-4-[(1-methylcyclopropyl)-carbonyl]-imino-1-phenylpyridazine; 6-methoxy-, 6-ethoxy-, 6-propoxy-, 6-isopropoxy-, 6-butoxy-, 6-isobutoxy- and 6-pentyloxy-1,4-dihydro-4-[(1-methylcyclopropyl)-carbonyl]-imino-1-phenylpyridazine; 1,4-dihydro-4-[(2-methylcyclopropyl)-carbonyl]-imino-1-phenylpyridazine; 6-methoxy-, 6-ethoxy-, 6-propoxy-, 6-isopropoxy-, 6-butoxy-, 6-isobutoxy- and 6-pentyloxy-1,4-dihydro-4-[(2-methylcyclopropyl)-carbonyl]-imino-1-phenylpyridazine; 1,4-dihydro-4-[(2,2-dimethylcyclopropyl)-carbonyl]-imino-1-phenylpyridazine; 6-methoxy-, 6-ethoxy-, 6-propoxy-, 6-isopropoxy-, 6-butoxy-, 6-isobutoxy- and 6-pentyloxy-1,4-dihydro-4-[(2,2-dimethylcyclopropyl)-carbonyl]-imino-1-phenylpyridazine; 4-(cyclobutylcarbonyl)-imino-1,4-dihydro-1-phenylpyridazine; 6-methoxy-, 6-ethoxy-, 6-propoxy-, 6-isopropoxy-, 6-butoxy-, 6-(sec.-butoxy)-, 6-isobutoxy-, 6-pentyloxy-, 6-hexyloxy- and 6-octyloxy-4-(cyclobutylcarbonyl)-imino-1,4-dihydro-1-phenylpyridazine; 1,4-dihydro-4-[(1-methylcyclobutyl)-carbonyl]-imino-1-phenylpyridazine; 6-methoxy-, 6-ethoxy-, 6-propoxy-, 6-butoxy- and 6-pentyloxy-1,4-dihydro-4-[(1-methylcyclobutyl)-carbonyl]-imino-1-phenylpyridazine; 4-(cyclopentylcarbonyl)-imino-1,4-dihydro-1-phenylpyridazine; 6-methoxy-, 6-ethoxy-, 6-propoxy-, 6-isopropoxy-, 6-butoxy-, 6-isobutoxy- and 6-pentyloxy-4-(cyclopentylcarbonyl)-imino-1,4-dihydro-1-phenylpyridazine; 4-(cyclohexylcarbonyl)-imino-1,4-dihydro-1-phenylpyridazine; 6-methoxy-, 6-ethoxy-, 6-propoxy-, 6-isopropoxy-, 6-butoxy- and 6-isobutoxy-4-(cyclohexylcarbonyl)-imino-1,4-dihydro-1-phenylpyridazine; 1,4-dihydro-4-[(1-methylcyclohexyl)-carbonyl]-imino-1-phenylpyridazine; 6-methoxy-, 6-ethoxy-, 6-propoxy- and 6-butoxy-1,4-dihydro-4-[(1-methylcyclohexyl)-carbonyl]-imino-1-phenylpyridazine; 4-(cycloheptylcarbonyl)-imino-1,4-dihydro-1-phenylpyridazine; 6-methoxy-, 6-ethoxy-, 6-propoxy-, 6-isopropoxy- and 6-butoxy-4-(cycloheptylcarbonyl)-imino-1,4-dihydro-1-phenylpyridazine; 4-(cyclooctylcarbonyl)-imino-1,4-dihydro-1-phenylpyridazine; 6-methoxy-, 6-ethoxy- and 6-propoxy-4-(cyclooctylcarbonyl)-imino-1,4-dihydro-1-phenylpyridazine; 4-acryloylimino-1,4-dihydro-1-phenylpyridazine; 6-methoxy-, 6-ethoxy-, 6-propoxy-, 6-isopropoxy-, 6-butoxy- and 6-octyloxy-4-acryloylimino-1,4-dihydro-1-phenyl-pyridazine; 1,4-dihydro-4-methacryloylimino-1-phenylpyridazine; 6-methoxy-, 6-ethoxy-, 6-propoxy- and 6-butoxy-1,4-dihydro-4-methacryloylimino-1-phenylpyridazine; 4-crotonoylimino-1,4-dihydro-1-phenylpyridazine; 6-methoxy-, 6-ethoxy-, 6-propoxy- and 6-butoxy-4-crotonoylimino-1,4-dihydro-1-phenylpyridazine; 1,4-dihydro-1-phenyl-4-[(vinylacetyl)-imino]-pyridazine; 6-methoxy-, 6-ethoxy- and 6-propoxy-1,4-dihydro-1-phenyl-4-[(vinylacetyl)-imino]-pyridazine; trans-1,4-dihydro-4-(2-methylbut-2-enoyl)-imino-1-phenylpyridazine; 6-methoxy-, 6-ethoxy- and 6-propoxy-trans-1,4-dihydro-4-(2-methylbut-2-enoyl)-imino-1-phenylpyridazine; 1,4-dihydro-4-(3,3-dimethylacryloyl)-imino-1-phenylpyridazine; 6-methoxy-, 6-ethoxy- and 6-propoxy-1,4-dihydro-4-(3,3-dimethylacryloyl)-imino-1-phenylpyridazine; trans-1,4-dihydro-4-(hex-2-enoyl)-imino-1-phenylpyridazine; 6-methoxy-, 6-ethoxy- and 6-propoxy-trans-1,4-dihydro-4-(hex-2-enoyl)-imino-1-phenylpyridazine; trans-1,4-dihydro-4-(hex-3-enoyl)-imino-1-phenylpyridazine; 6-methoxy- and 6-ethoxy-trans-1,4-dihydro-4-(hex-3-enoyl)-imino-1-phenylpyridazine; 4-benzoylimino-1,4-dihydro-1-phenylpyridazine; 6-methoxy-, 6-ethoxy-, 6-propoxy-, 6-isopropoxy-, 6-butoxy-, 6-(sec.-butoxy)-, 6-isobutoxy- and 6-octyloxy-4-benzoylimino-1,4-dihydro-1-phenylpyridazine; 1,4-dihydro-1-phenyl-4-[(2-toluoyl)-imino]-pyridazine; 6-methoxy-, 6-ethoxy- and 6-propoxy-1,4-dihydro-1-phenyl-4-[(2-toluoyl)-imino]-pyridazine; 1,4-dihydro-1-phenyl-4-[(3-toluoyl)-imino]-pyridazine; 6-methoxy-, 6-ethoxy- and 6-propoxy-1,4-dihydro-1-phenyl-4-[(3-toluoyl)-imino]-pyridazine; 1,4-dihydro-1-phenyl-4-[(4-toluoyl)-imino]-pyridazine; 6-methoxy-, 6-ethoxy- and 6-propoxy-1,4-dihydro-1-phenyl-4-[(4-toluoyl)-imino]-pyridazine; 1,4-dihydro-4-(2,4-dimethylbenzoyl)-imino-1-phenylpyridazine; 6-methoxy- and 6-ethoxy-1,4-dihydro-4-(2,4-dimethylbenzoyl)-imino-1-phenylpyridazine; 1,4-dihydro-4-(2-methoxybenzoyl)-imino-1-phenylpyridazine; 6-methoxy-, 6-ethoxy- and 6-propoxy-1,4-dihydro-4-(2-methoxybenzoyl)-imino-1-phenylpyridazine; 1,4-dihydro-4-(3-methoxybenzoyl)-imino-1-phenylpyridazine; 6-methoxy-, 6-ethoxy-, 6-propoxy- and 6-butoxy-1,4-dihydro-4-(3-methoxybenzoyl)-imino-1-phenylpyridazine; 1,4-dihydro-4-(4-methoxybenzoyl)-imino-1-phenylpyridazine; 6-methoxy-, 6-ethoxy-, 6-propoxy- and 6-butoxy-1,4-dihydro-4-(4-methoxybenzoyl)-imino-1-phenylpyridazine; 1,4-dihydro-4-(2,3-dimethoxybenzoyl)-imino-1-phenylpyridazine; 6-methoxy-, 6-ethoxy-, 6-propoxy- and 6-butoxy-1,4-dihydro-4-(2,3-dimethoxybenzoyl)-imino-1-phenylpyridazine; 1,4-dihydro-4-(2,4-dimethoxybenzoyl)-imino-1-phenylpyridazine; 6-methoxy-, 6-ethoxy-, 6-propoxy- and 6-butoxy-1,4-dihydro-4-(2,4-dimethoxybenzoyl)-imino-1-phenylpyridazine; 1,4-dihydro-4-(2,6-dimethoxybenzoyl)-imino-1-phenylpyridazine; 6-methoxy-, 6-ethoxy- and 6-propoxy-1,4-dihydro-4-(2,6-dimethoxybenzoyl)-imino-1-phenylpyridazine; 1,4-dihydro-4-(3,4-dimethoxybenzoyl)-imino-1-phenylpyridazine; 6-methoxy-, 6-ethoxy-, 6-propoxy- and 6-butoxy-1,4-dihydro-4-(3,4-dimethoxybenzoyl)-imino-1-phenylpyridazine; 1,4-dihydro-4-(3,5-dimethoxybenzoyl)-imino-1-phenylpyridazine; 6-methoxy-, 6-ethoxy-, 6-propoxy-, 6-butoxy- and 6-octyloxy-1,4-dihydro-4-(3,5-dimethoxybenzoyl)-imino-1-phenylpyridazine; 1,4-dihydro-1-phenyl-4-[(3,4,5-trimethoxybenzoyl)-imino]-pyridazine; 6-methoxy- and 6-ethoxy-1,4-dihydro-1-phenyl-4-[(3,4,5-trimethoxybenzoyl)-imino]-pyridazine; 4-(2-chlorobenzoyl)-imino-1,4-dihydro-1-phenylpyridazine; 6-methoxy-, 6-ethoxy- and 6-propoxy-4-(2-chlorobenzoyl)-imino-1,4-dihydro-1-phenylpyridazine; 4-(3-chlorobenzoyl)-imino-1,4-dihydro-1-phenylpyridazine; 6-methoxy-, 6-ethoxy-, 6-propoxy- and 6-butoxy-4-(3-chlorobenzoyl)-imino-1,4-dihydro-1-phenylpyridazine; 4-(4-chlorobenzoyl)-imino-1,4-dihydro-1-phenylpyridazine; 6-methoxy-, 6-ethoxy-, 6-propoxy-, 6-isopropoxy- and 6-butoxy-4-(4-chlorobenzoyl)-imino-1,4-dihydro-1-phenylpyridazine; 1,4-dihydro-4-(2-fluorobenzoyl)-imino-1-phenylpyridazine; 6-methoxy-, 6-ethoxy- and 6-propoxy-1,4-dihydro-4-(2-fluorobenzoyl)-imino-1-phenylpyridazine; 1,4-dihydro-4-(3-fluorobenzoyl)-imino-1-phenylpyridazine; 6-methoxy-, 6-ethoxy- and 6-propoxy-1,4-dihydro-4-(3-fluorobenzoyl)-imino-1-phenylpyridazine; 1,4-dihydro-4-(4-fluorobenzoyl)-imino-1-phenylpyridazine; 6-methoxy-, 6-ethoxy-, 6-propoxy- and 6-butoxy-1,4-dihydro-4-(4-fluorobenzoyl)-imino-1-phenylpyridazine; 4-(2,3-dichlorobenzoyl)-imino-1,4-dihydro-1-phenylpyridazine; 6-methoxy-, 6-ethoxy-, 6-propoxy- and 6-butoxy-4-(2,3-dichlorobenzoyl)-imino-1,4-dihydro-1-phenylpyridazine; 4-(2,4-dichlorobenzoyl)-imino-1,4-dihydro-1-phenylpyridazine; 6-methoxy-, 6-ethoxy-, 6-propoxy-, 6-isopropoxy-, 6-butoxy-, 6-isobutoxy- and 6-octyloxy-4-(2,4-dichlorobenzoyl)-imino-1,4-dihydro-1-phenylpyridazine; 4-(2,5-dichlorobenzoyl)-imino-1,4-dihydro-1-phenylpyridazine; 6-methoxy-, 6-ethoxy-, 6-propoxy- and 6-butoxy-4-(2,5-dichlorobenzoyl)-imino-1,4-dihydro-1-phenylpyridazine; 4-(2,6-dichlorobenzoyl)-imino-1,4-dihydro-1-phenylpyridazine; 6-methoxy-, 6-ethoxy-, 6-propoxy- and 6-butoxy-4-(2,6-dichlorobenzoyl)-imino-1,4-dihydro-1-phenylpyridazine; 4-(3,4-dichlorobenzoyl)-imino-1,4-dihydro-1-phenylpyridazine; 6-methoxy-, 6-ethoxy-, 6-propoxy- and 6-butoxy-4-(3,4-dichlorobenzoyl)-imino-1,4-dihydro-1-phenylpyridazine; 4-(3,5-dichlorobenzoyl)-imino-1,4-dihydro-1-phenylpyridazine; 6-methoxy-, 6-ethoxy-, 6-propoxy- and 6-butoxy-4-(3,5-dichlorobenzoyl)-imino-1,4-dihydro-1-phenylpyridazine; 4-(2,5-difluorobenzoyl)-imino-1,4-dihydro-1-phenylpyridazine; 6-methoxy-, 6-ethoxy-, 6-propoxy- and 6-butoxy-4-(2,5-difluorobenzoyl)-imino-1,4-dihydro-1-phenylpyridazine; 1,4-dihydro-1-phenyl-4-{[2-(trifluoromethyl)-benzoyl]-imino}-pyridazine; 6-methoxy-, 6-ethoxy- and 6-propoxy-1,4-dihydro-1-phenyl-4-{[2-(trifluoromethyl)-benzoyl]-imino}-pyridazine; 1,4-dihydro-1-phenyl-4-{[3-(trifluoromethyl)-benzoyl]-imino}-pyridazine; 6-methoxy-, 6-ethoxy-, 6-propoxy- and 6-butoxy-1,4-dihydro-1-phenyl-4-{[3-(trifluoromethyl)-benzoyl]-imino}-pyridazine; 1,4-dihydro-1-phenyl-4-{[4-(trifluoromethyl)-benzoyl]-imino}-pyridazine; 6-methoxy-, 6-ethoxy-, 6-propoxy- and 6-butoxy-1,4-dihydro-1-phenyl-4-{[4-(trifluoromethyl)-benzoyl]-imino}-pyridazine; 1,4-dihydro-4-(methoxycarbonyl)-imino-1-phenylpyridazine; 6-methoxy-, 6-ethoxy-, 6-propoxy-, 6-butoxy- and 6-octyloxy-1,4-dihydro-4-(methoxycarbonyl)-imino-1-phenylpyridazine; 1,4-dihydro-4-(ethoxycarbonyl)-imino-1-phenylpyridazine; 6-methoxy-, 6-ethoxy-, 6-propoxy-, 6-isopropoxy- and 6-butoxy-1,4-dihydro-4-(ethoxycarbonyl)-imino-1-phenylpyridazine; 1,4-dihydro-1-phenyl-4-[(propoxycarbonyl)-imino]-pyridazine; 6-methoxy-, 6-ethoxy-, 6-propoxy- and 6-butoxy-1,4-dihydro-1-phenyl-4-[(propoxycarbonyl)-imino]-pyridazine; 1,4-dihydro-4-(isopropoxycarbonyl)-imino-1-phenylpyridazine; 6-methoxy-, 6-ethoxy-, 6-propoxy- and 6-butoxy-1,4-dihydro-4-(isopropoxycarbonyl)-imino-1-phenylpyridazine; 4-(butoxycarbonyl)-imino-1,4-dihydro-1-phenylpyridazine; 6-methoxy-, 6-ethoxy-, 6-propoxy- and 6-butoxy-4-(butoxycarbonyl)-imino-1,4-dihydro-1-phenylpyridazine; 4-[(sec.-butoxy)-carbonyl]-imino-1,4-dihydro-1-phenylpyridazine; 6-methoxy-, 6-ethoxy-, 6-propoxy- and 6-butoxy-4-[(sec.-butoxy)-carbonyl]-imino-1,4-dihydro-1-phenylpyridazine; 1,4-dihydro-4-(isobutoxycarbonyl)-imino-1-phenylpyridazine; 6-methoxy-, 6-ethoxy-6-propoxy- and 6-butoxy-1,4-dihydro-4-(isobutoxycarbonyl)-imino-1-phenylpyridazine; 1,4-dihydro-4-(pentyloxycarbonyl)-imino-1-phenylpyridazine; 6-methoxy-, 6-ethoxy-, 6-propoxy- and 6-butoxy-1,4-dihydro-4-(pentyloxycarbonyl)-imino-1-phenylpyridazine; 1,4-dihydro-4-(hexyloxycarbonyl)-imino-1-phenylpyridazine; 6-methoxy-, 6-ethoxy-, 6-propoxy- and 6-butoxy-1,4-dihydro-4-(hexyloxycarbonyl)-imino-1-phenylpyridazine; 1,4-dihydro-4-(heptyloxycarbonyl)-imino-1-phenylpyridazine; 6-methoxy-, 6-ethoxy, 6-propoxy- and 6-butoxy-1,4-dihydro-4-(heptyloxycarbonyl)-imino-1-phenylpyridazine; 1,4-dihydro-4-(octyloxycarbonyl)-imino-1-phenylpyridazine; 6-methoxy-, 6-ethoxy-, 6-propoxy- and 6-butoxy-1,4-dihydro-4-(octyloxycarbonyl)-imino-1-phenylpyridazine; 4-(benzyloxycarbonyl)-imino-1,4-dihydro-1-phenylpyridazine; 6-methoxy-, 6-ethoxy-, 6-propoxy-, 6-butoxy- and 6-hexyloxy-4-(benzyloxycarbonyl)-imino-1,4-dihydro-1-phenylpyridazine; 1,4-dihydro-4-(p-methylbenzyloxycarbonyl)-imino-1-phenylpyridazine; 6-methoxy-, 6-ethoxy- and 6-propoxy-1,4-dihydro-4-(p-methylbenzyloxycarbonyl)-imino-1-phenylpyridazine; 1,4-dihydro-4-(p-methoxybenzyloxycarbonyl)-imino-1-phenylpyridazine; 6-methoxy-, 6-ethoxy- and 6-propoxy-1,4-dihydro-4-(p-methoxybenzyloxycarbonyl)-imino-1-phenylpyridazine; 1,4-dihydro-4-(m,p-dimethoxybenzyloxycarbonyl)-imino-1-phenylpyridazine; 6-methoxy-, 6-ethoxy- and 6-propoxy-1,4-dihydro-4-(m,p-dimethoxybenzyloxycarbonyl)-imino-1-phenylpyridazine; 4-(p-chlorobenzyloxycarbonyl)-imino-1,4-dihydro-1-phenylpyridazine; 6-methoxy-, 6-ethoxy-, 6-propoxy- and 6-butoxy-4-(p-chlorobenzyloxycarbonyl)-imino-1,4-dihydro-1-phenylpyridazine; 4-(o,p-dichlorobenzyloxycarbonyl)-imino-1,4-dihydro-1-phenylpyridazine; 6-methoxy-, 6-ethoxy-, 6-propoxy- and 6-butoxy-4-(o,p-dichlorobenzyloxycarbonyl)-imino-1,4-dihydro-1-phenylpyridazine; 1,4-dihydro-4-(p-fluorobenzyloxycarbonyl)-imino-1-phenylpyridazine; 6-methoxy-, 6-ethoxy- and 6-propoxy-1,4-dihydro-4-(p-fluorobenzyloxycarbonyl)-imino-1-phenylpyridazine; 1,4-dihydro-1-phenyl-4-{[m-(trifluoromethyl)-benzyloxycarbonyl]-imino}-pyridazine; 6methoxy-, 6-ethoxy- and 6-propoxy-1,4-dihydro-1-phenyl-4-{[m-(trifluoromethyl)-benzyloxycarbonyl]-imino}-pyridazine; 4-(allyloxycarbonyl)-imino-1,4-dihydro-1-phenylpyridazine; 6-methoxy-, 6-ethoxy-, 6-propoxy-, 6-butoxy- and 6-hexyloxy-4-(allyloxycarbonyl)-imino-1,4-dihydro-1-phenylpyridazine; 4-(but-2-enyloxycarbonyl)-imino-1,4-dihydro-1-phenylpyridazine; 6-methoxy-, 6-ethoxy- and 6-propoxy-4-(but-2-enyloxycarbonyl)-imino-1,4-dihydro-1-phenylpyridazine; 4-(but-3-enyloxycarbonyl)-imino-1,4-dihydro-1-phenylpyridazine; 6-methoxy-, 6-ethoxy- and 6-propoxy-4-(but-3-enyloxycarbonyl)-imino-1,4-dihydro-1-phenylpyridazine; 1,4-dihydro-4-(1-methylprop-2-enyloxycarbonyl)-imino-1-phenylpyridazine; 6-methoxy-, 6-ethoxy- and 6-propoxy-1,4-dihydro-4-(1-methylprop-2-enyloxycarbonyl)-imino-1-phenylpyridazine; 1,4-dihydro-4-(pent-4-enyloxycarbonyl)-imino-1-phenylpyridazine; 6-methoxy- and 6-ethoxy-1,4-dihydro-4-(pent-4-enyloxycarbonyl)-imino-1-phenylpyridazine; 1,4-dihydro-4-(phenoxycarbonyl)-imino-1-phenylpyridazine; 6-methoxy-, 6-ethoxy-, 6-propoxy- and 6-butoxy-1,4-dihydro-4-(phenoxycarbonyl)-imino-1-phenylpyridazine; 1,4-dihydro-1-phenyl-4-[(2-tolyloxycarbonyl)-imino]-pyridazine; 6-methoxy-, 6-ethoxy- and 6-propoxy-1,4-dihydro-1-phenyl-4-[(2-tolyloxycarbonyl)-imino]-pyridazine; 1,4-dihydro-1-phenyl-4-[(3-tolyloxycarbonyl)-imino]-pyridazine; 6-methoxy-, 6-ethoxy- and 6-propoxy-1,4-dihydro-1-phenyl-4-[(3-tolyloxycarbonyl)-imino]-pyridazine; 1,4-dihydro-1-phenyl-4-[(4-tolyloxycarbonyl)-imino]-pyridazine; 6-methoxy-, 6-ethoxy- and 6-propoxy-1,4-dihydro-1-phenyl-4-[(4-tolyloxycarbonyl)-imino]-pyridazine; 1,4-dihydro-4-(2-methoxyphenoxycarbonyl)-imino-1-phenylpyridazine; 6-methoxy-, 6-ethoxy- and 6-propoxy-1,4-dihydro-4-(2-methoxyphenoxycarbonyl)-imino-1-phenylpyridazine; 1,4-dihydro-4-(3-methoxyphenoxycarbonyl)-imino-1-phenylpyridazine; 6-methoxy-, 6-ethoxy-, 6-propoxy- and 6-butoxy-1,4-dihydro-4-(3-methoxyphenoxycarbonyl)-imino-1-phenylpyridazine; 1,4-dihydro-4-(4-methoxyphenoxycarbonyl)-imino-1-phenylpyridazine; 6-methoxy-, 6-ethoxy-, 6-propoxy- and 6-butoxy-1,4-dihydro-4-(4-methoxyphenoxycarbonyl)-imino-1-phenylpyridazine; 1,4-dihydro-4-(3,4-dimethoxyphenoxycarbonyl)-imino-1-phenylpyridazine; 6-methoxy-, 6-ethoxy-, 6-propoxy- and 6-butoxy-1,4-dihydro-4-(3,4-dimethoxyphenoxycarbonyl)-imino-1-phenylpyridazine; 1,4-dihydro-4-(3,5-dimethoxyphenoxycarbonyl)-imino-1-phenylpyridazine; 6-methoxy-, 6-ethoxy-, 6-propoxy- and 6-butoxy-1,4-dihydro-4-(3,5-dimethoxyphenoxycarbonyl)-imino-1-phenylpyridazine; 4-(2-chlorophenoxycarbonyl)-imino-1,4-dihydro-1-phenylpyridazine; 6-methoxy-, 6-ethoxy- and 6-propoxy-4-(2-chlorophenoxycarbonyl)-imino-1,4-dihydro-1-phenylpyridazine; 4-(3-chlorophenoxycarbonyl)-imino-1,4-dihydro-1-phenylpyridazine; 6-methoxy-, 6-ethoxy-, 6-propoxy- and 6-butoxy-4-(3-chlorophenoxycarbonyl)-imino-1,4-dihydro-1-phenylpyridazine; 4-(4-chlorophenoxycarbonyl)-imino-1,4-dihydro-1-phenylpyridazine; 6-methoxy-, 6-ethoxy-, 6-propoxy- and 6-butoxy-4-(4-chlorophenoxycarbonyl)-imino-1,4-dihydro-1-phenylpyridazine; 4-(2,4-dichlorophenoxycarbonyl)-imino-1,4-dihydro-1-phenylpyridazine; 6-methoxy-, 6-ethoxy-, 6-propoxy- and 6-butoxy-4-(2,4-dichlorophenoxycarbonyl)-imino-1,4-dihydro-1-phenylpyridazine; 4-(3,4-dichlorophenoxycarbonyl)-imino-1,4-dihydro-1-phenylpyridazine; 6-methoxy-, 6-ethoxy-, 6-propoxy- and 6-butoxy-4-(3,4-dichlorophenoxycarbonyl)-imino-1,4-dihydro-1-phenylpyridazine; 1,4-dihydro-4-(4-fluorophenoxycarbonyl)-imino-1-phenylpyridazine; 6-methoxy-, 6-ethoxy- and 6-propoxy-1,4-dihydro-4-(4-fluorophenoxycarbonyl)-imino-1-phenylpyridazine; 1,4-dihydro-1-phenyl-4-[3-(trifluoromethyl)-phenoxycarbonyl]-iminopyridazine; 6-methoxy-, 6-ethoxy- and 6-propoxy-1,4-dihydro-1-phenyl-4-{[3-(trifluoromethyl)-phenoxycarbonyl]-imino}-pyridazine; 1,4-dihydro-4-(methylmercaptocarbonyl)-imino-1-phenylpyridazine; 6-methoxy-, 6-ethoxy-, 6-propoxy- and 6-butoxy-1,4-dihydro-4-(methylmercaptocarbonyl)-imino-1-phenylpyridazine; 1,4-dihydro-4-(ethylmercaptocarbonyl)-imino-1-phenylpyridazine; 6-methoxy-, 6-ethoxy-, 6-propoxy- and 6-butoxy-1,4-dihydro-4-(ethylmercaptocarbonyl)-imino-1-phenylpyridazine; 1,4-dihydro-1-phenyl-4-[(propylmercaptocarbonyl)-imino]-pyridazine; 6-methoxy-, 6-ethoxy- and 6-propoxy-1,4-dihydro-1-phenyl-4-[(propylmercaptocarbonyl)-imino]-pyridazine; 1,4-dihydro-4-(isopropylmercaptocarbonyl)-imino-1-phenylpyridazine; 6-methoxy-, 6-ethoxy- and 6-propoxy-1,4-dihydro-4-(isopropylmercaptocarbonyl)-imino-1-phenylpyridazine; 4-(butylmercaptocarbonyl)-imino-1,4-dihydro-1-phenylpyridazine; 6-methoxy-, 6-ethoxy- and 6-propoxy-4-(butylmercaptocarbonyl)-imino-1,4-dihydro-1-phenylpyridazine; 1,4-dihydro-4-(pentylmercaptocarbonyl)-imino-1-phenylpyridazine; 6-methoxy-, 6-ethoxy- and 6-propoxy-1,4-dihydro-4-(pentylmercaptocarbonyl)-imino-1-phenylpyridazine; 1,4-dihydro-4-(hexylmercaptocarbonyl)-imino-1-phenylpyridazine; 6-methoxy-, 6-ethoxy- and 6-propoxy-1,4-dihydro-4-(hexylmercaptocarbonyl)-imino-1-phenylpyridazine; 1,4-dihydro-4-(heptylmercaptocarbonyl)-imino-1-phenylpyridazine; 6-methoxy-, 6-ethoxy- and 6-propoxy-1,4-dihydro-4-(heptylmercaptocarbonyl)-imino-1-phenylpyridazine; 4-(benzylmercaptocarbonyl)-imino-1,4-dihydro-1-phenylpyridazine; 6-methoxy-, 6-ethoxy-, 6-propoxy- and 6-butoxy-4-(benzylmercaptocarbonyl)-imino-1,4-dihydro-1-phenylpyridazine; 1,4-dihydro-4-(p-methylbenzylmercaptocarbonyl)-imino-1-phenylpyridazine; 6-methoxy- and 6-ethoxy-1,4-dihydro-4-(p-methylbenzylmercaptocarbonyl)-imino-1-phenylpyridazine; 1,4-dihydro-4-(p-methoxybenzylmercaptocarbonyl)-imino-1-phenylpyridazine; 6-methoxy- and 6-ethoxy-1,4-dihydro-4-(p-methoxybenzylmercaptocarbonyl)-imino-1-phenylpyridazine; 4-(p-chlorobenzylmercaptocarbonyl)-imino-1,4-dihydro-1-phenylpyridazine; 6-methoxy-, 6-ethoxy- and 6-propoxy-4-(p-chlorobenzylmercaptocarbonyl)-imino-1,4-dihydro-1-phenylpyridazine; 1,4-dihydro-4-(p-fluorobenzylmercaptocarbonyl)-imino-1-phenylpyridazine; 6-methoxy-, 6-ethoxy- and 6-propoxy-1,4-dihydro-4-(p-fluorobenzylmercaptocarbonyl)-imino-1-phenylpyridazine; 1,4-dihydro-1-phenyl-4-{[m-(trifluoromethyl)-benzylmercaptocarbonyl]-imino}-pyridazine; 6-methoxy- and 6-ethoxy-1,4-dihydro-1-phenyl-4-{[m-(trifluoromethyl)-benzylmercaptocarbonyl]-imino}-pyridazine; 4-(allylmercaptocarbonyl)-imino-1,4-dihydro-1-phenylpyridazine; 6-methoxy-, 6-ethoxy- and 6-propoxy-4-(allylmercaptocarbonyl)-imino-1,4-dihydro-1-phenylpyridazine; 4-(but-2-enylmercaptocarbonyl)-imino-1,4-dihydro-1-phenylpyridazine; 6-methoxy- and 6-ethoxy-4-(but-2-enylmercaptocarbonyl)-imino-1,4-dihydro-1-phenylpyridazine; 4-(but-3-enylmercaptocarbonyl)-imino-1,4-dihydro-1-phenylpyridazine; 6-methoxy- and 6-ethoxy-4-(but-3-enylmercaptocarbonyl)-imino-1,4-dihydro-1-phenylpyridazine; 1,4-dihydro-1-phenyl-4-[(phenylmercaptocarbonyl)-imino]-pyridazine; 6-methoxy-, 6-ethoxy- and 6-propoxy-1,4-dihydro-1-phenyl-4-[(phenylmercaptocarbonyl)-imino]-pyridazine; 1,4-dihydro-1-phenyl-4-[(4-tolylmercaptocarbonyl)-imino]-pyridazine; 6-methoxy- and 6-ethoxy-1,4-dihydro-1-phenyl-4-[(4-tolylmercaptocarbonyl)-imino]-pyridazine; 1,4-dihydro-4-(4-methoxyphenylmercaptocarbonyl)-imino-1-phenylpyridazine; 6-methoxy- and 6-ethoxy-1,4-dihydro-4-(4-methoxyphenylmercaptocarbonyl)-imino-1-phenylpyridazine; 4-(4-chlorophenylmercaptocarbonyl)-imino-1,4-dihydro-1-phenylpyridazine; 6-methoxy-, 6-ethoxy- and 6-propoxy-4-(4-chlorophenylmercaptocarbonyl)-imino-1,4-dihydro-1-phenylpyridazine; 1,4-dihydro-4-(4-fluorophenylmercaptocarbonyl)-imino-1-phenylpyridazine; 6-methoxy- and 6-ethoxy-1,4-dihydro-4-(4-fluorophenylmercaptocarbonyl)-imino-1-phenylpyridazine; 1,4-dihydro-1-phenyl-4-{[3-(trifluoromethyl)-phenylmercaptocarbonyl]-imino}-pyridazine; 6-methoxy- and 6-ethoxy-1,4-dihydro-1-phenyl-4-{[3-(trifluoromethyl)-phenylmercaptocarbonyl]-imino}-pyridazine; 1,4-dihydro-4-(methylcarbamyl)-imino-1-phenylpyridazine; 6-methoxy-, 6-ethoxy-, 6-propoxy-, 6-isopropoxy-, 6-butoxy-, 6-(sec.-butoxy)-, 6-isobutoxy-, 6-pentyloxy-, 6-octyloxy-1,4-dihydro-4-(methylcarbamyl)-imino-1-phenylpyridazine; 1,4-dihydro-4-(ethylcarbamyl)-imino-1-phenylpyridazine; 6-methoxy-, 6-ethoxy-, 6-propoxy-, 6-isopropoxy-, 6-butoxy- and 6-pentyloxy-1,4-dihydro-4-(ethylcarbamyl)-imino-1-phenylpyridazine; 1,4-dihydro-1-phenyl-4-[(propylcarbamyl)-imino]-pyridazine; 6-methoxy-, 6-ethoxy-, 6-propoxy-, 6-isopropoxy- and 6-butoxy-1,4-dihydro-1-phenyl-4-[(propylcarbamyl)-imino]-pyridazine; 1,4-dihydro-4-(isopropylcarbamyl)-imino-1-phenylpyridazine; 6-methoxy-, 6-ethoxy-, 6-propoxy-, 6-isopropoxy- and 6-butoxy-1,4-dihydro-4-(isopropylcarbamyl)-imino-1-phenylpyridazine; 4-(butylcarbamyl)-imino-1,4-dihydro-1-phenylpyridazine; 6-methoxy-, 6-ethoxy-, 6-propoxy- and 6-butoxy-4-(butylcarbamyl)-imino-1,4-dihydro-1-phenylpyridazine; 4-[(sec.-butyl)-carbamyl]-imino-1,4-dihydro-1-phenylpyridazine; 6-methoxy-, 6-ethoxy-, 6-propoxy- and 6-butoxy-4-[(sec.-butyl)-carbamyl]-imino-1,4-dihydro-1-phenylpyridazine; 1,4-dihydro-4-(isobutylcarbamyl)-imino-1-phenylpyridazine; 6-methoxy-, 6-ethoxy-, 6-propoxy- and 6-butoxy-1,4-dihydro-4-(isobutylcarbamyl)-imino-1-phenylpyridazine; 4-[(tert.-butyl)-carbamyl]-imino-1,4-dihydro-1-phenylpyridazine; 6-methoxy-, 6-ethoxy-, 6-propoxy- and 6-butoxy-4-[(tert.-butyl)-carbamyl]-imino-1,4-dihydro-1-phenylpyridazine; 1,4-dihydro-4-(pentylcarbamyl)-imino-1-phenylpyridazine; 6-methoxy-, 6-ethoxy-, 6-propoxy-, and 6-butoxy-1,4-dihydro-4-(pentylcarbamyl)-imino-1-phenylpyridazine; 1,4-dihydro-4-(hexylcarbamyl)-imino-1-phenylpyridazine; 6-methoxy-, 6-ethoxy-, 6-propoxy- and 6-butoxy-1,4-dihydro-4-(hexylcarbamyl)-imino-1-phenylpyridazine; 1,4-dihydro-4-(heptylcarbamyl)-imino-1-phenylpyridazine; 6-methoxy-, 6-ethoxy-, 6-propoxy- and 6-butoxy-1,4-dihydro-4-(heptylcarbamyl)-imino-1-phenylpyridazine; 1,4-dihydro-4-(octylcarbamyl)-imino-1-phenylpyridazine; 6-methoxy-, 6-ethoxy-, 6-propoxy- and 6-butoxy-1,4-dihydro-4-(octylcarbamyl)-imino-1-phenylpyridazine; 4-(benzylcarbamyl)-imino-1,4-dihydro-1-phenylpyridazine; 6-methoxy-, 6-ethoxy-, 6-propoxy- and 6-butoxy-4-(benzylcarbamyl)-imino-1,4-dihydro-1-phenylpyridazine; 1,4-dihydro-4-(p-methylbenzylcarbamyl)-imino-1-phenylpyridazine; 6-methoxy-, 6-ethoxy- and 6-propoxy-1,4-dihydro-4-(p-methylbenzylcarbamyl)-imino-1-phenylpyridazine; 1,4-dihydro-4-(m-methoxybenzylcarbamyl)-imino-1-phenylpyridazine; 6-methoxy-, 6-ethoxy- and 6-propoxy-1,4-dihydro-4-(m-methoxybenzylcarbamyl)-imino-1-phenylpyridazine; 1,4-dihydro-4-(p-methoxybenzylcarbamyl)-imino-1-phenylpyridazine; 6-methoxy-, 6-ethoxy- and 6-propoxy-1,4-dihydro-4-(p-methoxybenzylcarbamyl)-imino-1-phenylpyridazine; 4-(m-chlorobenzylcarbamyl)-imino-1,4-dihydro-1-phenypyridazine; 6-methoxy-, 6-ethoxy- and 6-propoxy-4-(m-chlorobenzylcarbamyl)-imino-1,4-dihydro-1-phenylpyridazine; 4-(p-chlorobenzylcarbamyl)-imino-1,4-dihydro-1-phenylpyridazine; 6-methoxy-, 6-ethoxy- and 6-propoxy-4-(p-chlorobenzylcarbamyl)-imino-1,4-dihydro-1-phenylpyridazine; 1,4-dihydro-4-(p-fluorobenzylcarbamyl)-imino-1-phenylpyridazine; 6-methoxy-, 6-ethoxy- and 6-propoxy-1,4-dihydro-4-(p-fluorobenzylcarbamyl)-imino-1-phenylpyridazine; 1,4-dihydro-1-phenyl-4-{[m-(trifluoromethyl)-benzylcarbamyl]-imino}-pyridazine; 6-methoxy-, 6-ethoxy- and 6-propoxy-1,4-dihydro-1-phenyl-4-{[m-(trifluoromethyl)-benzylcarbamyl]-imino}-pyridazine; 1,4-dihydro-1-phenyl-4-[(phenylcarbamyl)-imino]-pyridazine; 6-methoxy-, 6-ethoxy-, 6-propoxy-, 6-isopropoxy- and 6-butoxy-1,4-dihydro-1-phenyl-4-[(phenylcarbamyl)-imino]-pyridazine; 1,4-dihydro-1-phenyl-4-[(m-tolylcarbamyl)-imino]-pyridazine; 6-methoxy- and 6-ethoxy-1,4-dihydro-1-phenyl-4-[(m-tolylcarbamyl)-imino]-pyridazine; 1,4-dihydro-1-phenyl-4-[(p-tolylcarbamyl)-imino]-pyridazine; 6-methoxy- and 6-ethoxy-1,4-dihydro-1-phenyl-4-[(p-tolylcarbamyl)-imino]-pyridazine; 1,4-dihydro-4-(o-methoxyphenylcarbamyl)-imino-1-phenylpyridazine; 6-methoxy- and 6-ethoxy-1,4-dihydro-4-(o-methoxyphenylcarbamyl)-imino-1-phenylpyridazine; 1,4-dihydro-4-(m-methoxyphenylcarbamyl)-imino-1-phenylpyridazine; 6-methoxy- and 6-ethoxy-1,4-dihydro-4-(m-methoxyphenylcarbamyl)-imino-1-phenylpyridazine; 1,4-dihydro-4-(p-methoxyphenylcarbamyl)-imino-1-phenylpyridazine; 6-methoxy- and 6-ethoxy-1,4-dihydro-4-(p-methoxyphenylcarbamyl)-imino-1-phenylpyridazine; 1,4-dihydro-4-(o,p-dimethoxyphenylcarbamyl)-imino-1-phenylpyridazine; 6-methoxy- and 6-ethoxy-1,4-dihydro-4-(o,p-dimethoxyphenylcarbamyl)-imino-1-phenylpyridazine; 1,4-dihydro-4-[(2,5-dimethoxyphenyl)-carbamyl]-imino-1-phenylpyridazine; 6-methoxy- and 6-ethoxy-1,4-dihydro-4-[(2,5-dimethoxyphenyl)-carbamyl]-imino-1-phenylpyridazine; 4-(o-chlorophenylcarbamyl)-imino-1,4-dihydro-1-phenylpyridazine; 6-methoxy- and 6-ethoxy-4-(o-chlorophenylcarbamyl)-imino-1,4-dihydro-1-phenylpyridazine; 4-(m-chlorophenylcarbamyl)-imino-1,4-dihydro-1-phenylpyridazine; 6-methoxy- and 6-ethoxy-4-(m-chlorophenylcarbamyl)-imino-1,4-dihydro-1-phenylpyridazine; 4-(p-chlorophenylcarbamyl)-imino-1,4-dihydro-1-phenylpyridazine; 6-methoxy- and 6-ethoxy-4-(p-chlorophenylcarbamyl)-imino-1,4-dihydro-1-phenylpyridazine; 4-[2,3-dichlorophenyl)-carbamyl]-imino-1,4-dihydro-1-phenylpyridazine; 6-methoxy- and 6-ethoxy-4-[(2,3-dichlorophenyl)-carbamyl]-imino-1,4-dihydro-1-phenylpyridazine; 4-[(3,4-dichlorophenyl)-carbamyl]-imino-1,4-dihydro-1-phenylpyridazine; 6-methoxy- and 6-ethoxy-4-[(3,4-dichlorophenyl)-carbamyl]-imino-1,4-dihydro-1-phenylpyridazine; 4-(m,m-dichlorophenylcarbamyl)-imino-1,4-dihydro-1-phenylpyridazine; 6-methoxy- and 6-ethoxy-4-(m,m-dichlorophenylcarbamyl)-imino-1,4-dihydro-1-phenylpyridazine; 1,4-dihydro-4-(p-fluorophenylcarbamyl)-imino-1-phenylpyridazine; 6-methoxy- and 6-ethoxy-1,4-dihydro-4-(p-fluorophenylcarbamyl)-imino-1-phenylpyridazine; 1,4-dihydro-1-phenyl-4-{[o-(trifluoromethyl)-phenylcarbamyl]-imino}-pyridazine; 6-methoxy- and 6-ethoxy-1,4-dihydro-1-phenyl-4-{[o-(trifluoromethyl)-phenylcarbamyl]-imino}-pyridazine; 1,4-dihydro-1-phenyl-4-{[m-(trifluoromethyl)-phenylcarbamyl]-imino}-pyridazine; 6-methoxy- and 6-ethoxy-1,4-dihydro-1-phenyl-4-{[m-(trifluoromethyl)-phenylcarbamyl]-imino}-pyridazine; 1,4-dihydro-4-(methylthiocarbamyl)-imino-1-phenylpyridazine; 6-methoxy-, 6-ethoxy-, 6-propoxy-, 6-isopropoxy-, 6-but-oxy-, 6-(sec.-butoxy)-, 6-isobutoxy-, 6-pentyloxy- and 6-octyloxy-1,4-dihydro-4-(methylthiocarbamyl)-imino-1-phenylpyridazine; 1,4-dihydro-4-(ethylthiocarbamyl)-imino-1-phenylpyridazine; 6-methoxy-, 6-ethoxy-, 6-propoxy-, 6-isopropoxy-, 6-butoxy- and 6-pentyloxy-1,4-dihydro-4-(ethylthiocarbamyl)-imino-1-phenylpyridazine; 1,4-dihydro-1-phenyl-4-[(propylthiocarbamyl)-imino]-pyridazine; 6-methoxy-, 6-ethoxy-, 6-propoxy-, 6-isopropoxy- and 6-butoxy-1,4-dihydro-1-phenyl-4-[(propylthiocarbamyl)-imino]-pyridazine; 1,4-dihydro-4-(isopropylthiocarbamyl)-imino-1-phenylpyridazine; 6-methoxy-, 6-ethoxy-, 6-propoxy-, 6-isopropoxy- and 6-butoxy-1,4-dihydro-4-(isopropylthiocarbamyl)-imino-1-phenylpyridazine; 4-(butylthiocarbamyl)-imino-1,4-dihydro-1-phenylpyridazine; 6-methoxy-, 6-ethoxy-, 6-propoxy-, 6-isopropoxy- and 6-butoxy-4-(butylthiocarbamyl)-imino-1,4-dihydro-1-phenylpyridazine; 4-[(sec.-butyl)-thiocarbamyl]-imino-1,4-dihydro-1-phenylpyridazine; 6-methoxy-, 6-ethoxy- and 6-propoxy-4-[(sec.-butyl)-thiocarbamyl]-imino-1,4-dihydro-1-phenylpyridazine; 1,4-dihydro-4-(isobutylthiocarbamyl)-imino-1-phenylpyridazine; 6-methoxy-, 6-ethoxy- and 6-propoxy-1,4-dihydro-4-(isobutylthiocarbamyl)-imino-1-phenylpyridazine; 1,4-dihydro-4-(pentylthiocarbamyl)-imino-1-phenylpyridazine; 6-methoxy-, 6-ethoxy-, 6-propoxy- and 6-butoxy-1,4-dihydro-4-(pentylthiocarbamyl)-imino-1-phenylpyridazine; 1,4-dihydro-4-(hexylthiocarbamyl)-imino-1-phenylpyridazine; 6-methoxy-, 6-ethoxy-, 6-propoxy- and 6-butoxy-1,4-dihydro-4-(hexylthiocarbamyl)-imino-1-phenylpyridazine; 1,4-dihydro-4-(heptylthiocarbamyl)-imino-1-phenylpyridazine; 6-methoxy-, 6-ethoxy-, 6-propoxy- and 6-butoxy-1,4-dihydro-4-(heptylthiocarbamyl)-imino-1-phenylpyridazine; 4-(benzylthiocarbamyl)-imino-1,4-dihydro-1-phenylpyridazine; 6-methoxy-, 6-ethoxy- and 6-propoxy-4-(benzylthiocarbamyl)-imino-1,4-dihydro-1-phenylpyridazine; 1,4-dihydro-4-(p-methylbenzylthiocarbamyl)-imino-1-phenylpyridazine; 6-methoxy-, 6-ethoxy- and 6-propoxy-1,4-dihydro-4-(p-methylbenzylthiocarbamyl)-imino-1-phenylpyridazine; 1,4-dihydro-4-(m-methoxybenzylthiocarbamyl)-imino-1-phenylpyridazine; 6-methoxy-, 6-ethoxy- and 6-propoxy-1,4-dihydro-4-(m-methoxybenzylthiocarbamyl)-imino-1-phenylpyridazine; 4-(p-chlorobenzylthiocarbamyl)-imino-1,4-dihydro-1-phenylpyridazine; 6-methoxy-, 6-ethoxy- and 6-propoxy-4-(p-chlorobenzylthiocarbamyl)-imino-1,4-dihydro-1-phenylpyridazine; 1,4-dihydro-1-phenyl-4-{[m-(trifluoromethyl)-benzylthiocarbamyl]-imino}-pyridazine; 6-methoxy-, 6-ethoxy- and 6-propoxy-1,4-dihydro-1-phenyl-4-{[m-(trifluoromethyl)-benzylthiocarbamyl]-imino}-pyridazine; 1,4-dihydro-1-phenyl-4-[(phenylthiocarbamyl)-imino]-pyridazine; 6-methoxy-, 6-ethoxy- and 6-propoxy-1,4-dihydro-1-phenyl-4-[(phenylthiocarbamyl)-imino]-pyridazine; 1,4-dihydro-1-phenyl-4-[(p-tolylthiocarbamyl)-imino]-pyridazine; 6-methoxy-, 6-ethoxy- and 6-propoxy-1,4-dihydro-1-phenyl-4-[(p-tolylthiocarbamyl)-imino]-pyridazine; 1,4-dihydro-4-(m-methoxyphenylthiocarbamyl)-imino-1-phenylpyridazine; 6-methoxy-, 6-ethoxy- and 6-propoxy-1,4-dihydro-4-(m-methoxyphenylthiocarbamyl-imino-1-phenylpyridazine; 4-(p-chlorophenylthiocarbamyl-imino-1,4-dihydro-1-phenylpyridazine; 6-methoxy-, 6-ethoxy- and 6-propoxy-4-(p-chlorophenylthiocarbamyl-imino-1,4-dihydro-1-phenylpyridazine; 1,4-dihydro-4-(m-fluorophenylthiocarbamyl-imino-1-phenylpyridazine; 6-methoxy-, 6-ethoxy- and 6-propoxy-1,4-dihydro-4-(m-fluorophenylthiocarbamyl)-imino-1-phenylpyridazine; 1,4-dihydro-4-(p-fluorophenylthiocarbamyl-imino-1-phenylpyridazine; 6-methoxy- 6-ethoxy- and 6-propoxy-1,4-dihydro-4-(p-fluorophenylthiocarbamyl-imino-1-phenylpyridazine; 1,4-dihydro-4-(methoxyoxalyl)-imino-1-phenylpyridazine; 6-methoxy-, 6-ethoxy-, 6-propoxy-, 6-isopropoxy-, 6-butoxy- and 6-octyloxy-1,4-dihydro-4-(methoxyoxalyl)-imino-1-phenylpyridazine; 1,4-dihydro-4-(ethoxyoxalyl)-imino-1-phenylpyridazine; 6-methoxy-, 6-ethoxy-, 6-propoxy-, 6-isopropoxy-, 6-butoxy-, 6-(sec.-butoxy)-, 6-isobutoxy- and 6-pentyloxy-1,4-dihydro-4-(ethoxyoxalyl)-imino-1-phenylpyridazine; 1,4-dihydro-1-phenyl-4-[(propoxyoxalyl)-imino]-pyridazine; 6-methoxy-, 6-ethoxy-, 6-propoxy-, 6-isopropoxy- and 6-but-oxy-1,4-dihydro-1-phenyl-4-[(propoxyoxalyl)-imino]-pyridazine; 1,4-dihydro-4-(isopropoxyoxalyl)-imino-1-phenylpyridazine; 6-methoxy-, 6-ethoxy-, 6-propoxy and 6-but-oxy-1,4-dihydro-4-(isopropoxyoxalyl)-imino-1-phenylpyridazine; 4-(butoxyoxalyl)-imino-1,4-dihydro-1-phenylpyridazine; 6-methoxy-, 6-ethoxy-, 6-propoxy- and 6-butoxy-4-(butoxyoxalyl)-imino-1,4-dihydro-1-phenylpyridazine; 4-[(sec.-butoxy)-oxalyl]-imino-1,4-dihydro-1-phenylpyridazine; 6-methoxy-, 6-ethoxy-, 6-propoxy- and 6-butoxy-4-[(sec.-butoxy)-oxalyl]-imino-1,4-dihydro-1-phenylpyridazine; 1,4-dihydro-4-(isobutoxyoxalyl)-imino-1-phenylpyridazine; 6-methoxy-, 6-ethoxy-, 6-propoxy- and 6-butoxy-1,4-dihydro-4-(isobutoxyoxalyl)-imino-1-phenylpyridazine; 4-[(tert.-butoxy)-oxalyl]-imino-1,4-dihydro-1-phenylpyridazine; 6-methoxy-, 6-ethoxy-, 6-propoxy- and 6-butoxy-4-[(tert.-butoxy)-oxalyl]-imino-1,4-dihydro-1-phenylpyridazine; 1,4-dihydro-1-phenyl-4-[(pentyloxyoxalyl)-imino]-pyridazine; 6-methoxy-, 6-ethoxy-, 6-propoxy- and 6-butoxy-1,4-dihydro-1-phenyl-4-[(pentyloxyoxalyl)-imino]-pyridazine; 1,4-dihydro-4-(hexyloxyoxalyl)-imino-1-phenylpyridazine; 6-methoxy-, 6-ethoxy-, 6-propoxy- and 6-butoxy-1,4-dihydro-4-(hexyloxyoxalyl)-imino-1-phenylpyridazine; 1,4-dihydro-4-(heptyloxyoxalyl)-imino-1-phenylpyridazine; 6-methoxy-, 6-ethoxy-, 6-propoxy- and 6-butoxy-1,4-dihydro-4-(heptyloxyoxalyl)-imino-1-phenylpyridazine; 1,4-dihydro-4-(octyloxyoxalyl)-imino-1-phenylpyridazine; and 6-methoxy-, 6-ethoxy-, 6-propoxy- and 6-butoxy-1,4-dihydro-4-(octyloxyoxalyl)-imino-1-phenylpyridazine; and their addition salts with physiologically tolerated acids.

It should be pointed out that the substituted imino radical in the compounds of the formula (I) may give rise to syn and anti isomers. The present invention relates in each case to both these isomers and to mixtures of these.

In the case of certain radicals $R^1$, eg. (2-methylcyclopropyl)-carbonyl, cis/trans isomerism occurs. The present invention relates in each case to both these isomers and to mixtures of these. The pure cis or trans compounds are advantageously obtained by using pure starting compounds, or by separating the mixture of the cis and trans compounds by crystallization.

The novel compounds and their addition salts with physiologically tolerated acids are useful as drugs, having an antidepressive or hypertensive action, for the treatment of psychological disturbances, in particular depression, and circulatory disturbances associated with hypotonia.

The pharmacological properties were investigated using the following methods: Antidepressive action:

Reserpine (2.15 mg/kg, administered subcutaneously) reduces the body temperature of male Swiss mice weighing 20-26 g by 3° C. on average, measured 2 hours after the administration of reserpine and at an ambient temperature of from 20° to 22° C. Antidepressants effect dose-dependent inhibition of this hypothermia. The test substances are administered orally 60 minutes before the administration of reserpine.

The dose which effects 50% inhibition of the reserpine-induced hypothermia is determined, as the ED 50%, from the linear regression between log dose (mg/kg) and relative reduction in hypothermia (Δ%). Effect on the blood pressure:

The hypertensive action was demonstrated on pithed male Sprague-Dawley rats weighing 200-280 g. The measurement of the blood pressure in the carotid artery was carried out by means of Statham transducers. The substance was administered in the jugular vein (as an aqueous solution, 1 ml/kg) or intraperitoneally (as a tragacanth suspension, 2 ml/kg). The ED 20% is determined as the dose which increases the blood pressure by 20%.

The results found are summarized in Tables 1 and 2, the doses given being based on the base in each case. Amezinium metil-sulfate (1-phenyl-4-amino-6-methoxypyridazinium methosulfate, German Pat. No. 1,912,941), which is an established drug, and the compound from Example 1 of German Laid-Open Application DOS No. 2,245,248 (1-phenyl-4-aminopyridazinium perchlorate) were employed for comparison, these compounds being conventional and structurally similar compounds.

Both compounds have an antidepressive and hypertensive action. In the case of amezinium, the quotient ED 50% antidepressive action/ED 20%, hypertensive action is 14.7 when the test for hypertensive action is carried out after intravenous administration, and 1.98 when this test is carried out after intraperitoneal administration, while the corresponding values for the compound from Example 1 of German Laid-Open Application DOS No. 2,245,248 are 22.2 and 1.6 respectively, as can be seen from Table 1.

The novel compounds exhibit pronounced selectively; either the antidepressive action or the hypertensive action is more strongly pronounced, resulting in a particular, unforeseeable action profile in one of these directions of action. This is evident from the fact that the quotient defined above differs wtih respect to the comparative compounds. If the quotient becomes smaller, this indicates an antidepressive action which is more pronounced than the hypertensive action, hence a more selective antidepressive action. When the quotient becomes larger, this indicates a hypertensive action which is more pronounced than the antidepressive action, hence a more selective hypertensive action. This arises, inter alia, from the fact that the hypertensive ED 20 constitutes the denominator of the quotient. It is possible that the unforeseeable selective direction of action is attributable to the special substitution, in accordance with the invention, at the 4-imino group.

The compounds in Table 1 show a more selective antidepressive action than the reference substances, the antidepressive action being measured on the inhibition of the reserpine-induced hypothermia. The quotient of antidepressive action and hypertensive action is smaller by a factor of no less than two, at maximum by a factor of from 52 to 77 (Examples 85 and 31), than in the case of amezinium.

The compounds of Table 2 are particularly effective hypertensive agents. The blood pressure is increased by doses (ED 20%) which are smaller than the antidepressive effective dose (ED 50%) by as much as a factor of 24 (Example 14) to a factor of 120 (Example 30). In the case of the reference substances, the hypertensive doses are smaller by factors of only 15 (amezinium) and 22.

TABLE 1

| Example No. | Reserpine antagonism, hypothermia of the mouse, oral administration ED 50% (1) | | Hypertensive action, pithed rat | | | | Q (4) | |
|---|---|---|---|---|---|---|---|---|
| | | | i.v. administration ED 20% (3) | | i.p. administration ED 20% (3) | | | |
| | mg/kg | R.A. (2) | mg/kg | R.A. | mg/kg | R.A. (2) | (i.v.) | (i.p.) |
| 1 | 0.67 | 1.09 | 0.32 | 0.16 | | | 2.09 | |
| 3 | 0.33 | 2.22 | 0.20 | 0.25 | | | 1.65 | |
| 5 | 0.40 | 1.83 | 0.215 | 0.23 | | | 1.82 | |
| 10 | 1.41 | 0.52 | 0.464 | 0.11 | | | 3.04 | |
| 15 | 2.7 | 0.27 | | | >10 | <0.04 | | <0.27 |
| 19 | 1.35 | 0.54 | | | >10 | <0.04 | | <0.14 |
| 20 | 1.1 | 0.67 | | | >10 | <0.04 | | <0.11 |
| 22 | 3.1 | 0.24 | | | 4.64 | 0.08 | | 0.67 |
| 23 | 0.98 | 0.74 | | | 1.0 | 0.37 | | 0.98 |
| 26 | 3.26 | 0.22 | | | 4.64 | 0.08 | | 0.70 |

TABLE 1-continued

| Example No. | Reserpine antagonism, hypothermia of the mouse, oral administration ED 50% (1) | | Hypertensive action, pithed rat | | | | Q (4) | |
|---|---|---|---|---|---|---|---|---|
| | | | i.v. administration ED 20% (3) | | i.p. administration ED 20% (3) | | | |
| | mg/kg | R.A. (2) | mg/kg | R.A. | mg/kg | R.A. (2) | (i.v.) | (i.p.) |
| 28 | 0.58 | 1.26 | 0.1 | 0.50 | | | 5.80 | |
| 29 | 0.86 | 0.85 | 0.215 | 0.23 | | | 4.00 | |
| 31 | 0.28 | 2.62 | 1.47 | 0.03 | | | 0.19 | |
| 34 | 0.71 | 1.03 | 0.1 | 0.50 | | | 7.10 | |
| 35 | 0.25 | 2.93 | 0.1 | 0.50 | | | 2.50 | |
| 36 | 2.0 | 0.37 | 0.316 | 0.16 | | | 6.33 | |
| 37 | 0.7 | 1.05 | 1.0 | 0.05 | | | 0.70 | |
| 48 | 1.1 | 0.67 | | | 6.81 | 0.05 | | 0.16 |
| 49 | 1.71 | 0.43 | | | 4.64 | 0.08 | | 0.37 |
| 50 | 0.18 | 4.07 | | | 3.16 | 0.12 | | 0.06 |
| 52 | 1.4 | 0.52 | | | 3.16 | 0.12 | | 0.44 |
| 60 | 0.93 | 0.79 | | | 2.15 | 0.17 | | 0.43 |
| 62 | 0.66 | 1.11 | 0.56 | 0.09 | | | 1.18 | |
| 64 | 1.27 | 0.58 | >10 | <0.04 | | | | <0.13 |
| 66 | 1.8 | 0.41 | >10 | <0.04 | | | | <0.18 |
| 68 | 0.95 | 0.77 | >21.5 | <0.02 | | | | <0.04 |
| 69 | 4.86 | 0.15 | 2.15 | 0.02 | | | 2.26 | |
| 71 | 0.76 | 0.96 | 0.464 | 0.11 | | | 1.64 | |
| 72 | 1.47 | 0.50 | 0.464 | 0.11 | | | 3.17 | |
| 73 | 1.23 | 0.60 | >10 | <0.04 | | | | <0.12 |
| 74 | 8.45 | 0.09 | 4.64 | 0.01 | | | 1.82 | |
| 77 | 3.40 | 0.22 | | | 3.16 | 0.12 | | 1.08 |
| 78 | 0.73 | 1.00 | | | 10 | 0.04 | | 0.07 |
| 79 | 1.14 | 0.64 | | | 10 | 0.04 | | 0.11 |
| 80 | 1.5 | 0.49 | >10 | <0.04 | | | | <0.15 |
| 84 | 0.37 | 1.98 | 0.464 | 0.11 | | | 0.80 | |
| 85 | 0.28 | 2.62 | 1.0 | 0.05 | | | 0.28 | |
| 86 | 2.1 | 0.35 | >1.0 | <0.05 | | | <2.1 | |
| 87 | 2.91 | 0.25 | >1.0 | <0.05 | | | <2.91 | |
| Amezinium | 0.733 | 1.00 | 0.05 | 1.00 | 0.37 | 1.00 | 14.66 | 1.98 |
| German Laid-Open Application DOS 2,245,248 Example 1 | 0.40 | 1.83 | 0.018 | 2.78 | 0.25 | 1.48 | 22.22 | 1.60 |

(1) Dose which inhibits the reserpine-induced hypothermia of the mouse by 50%
(2) Relative activity: amezinium = 1.00
(3) Dose which increases the blood pressure of the pithed rat by 20%
(4) $Q = \dfrac{\text{ED 50\%, reserpine antagonism}}{\text{ED 20\%, hypertensive action}}$

TABLE 2

| Example No. | Hypertensive action, pithed rat ED 20% (1) | | Reserpine antagonism, hypothermia of the mouse, oral administration ED 50% (3) | | Q (4) Increase |
|---|---|---|---|---|---|
| | mg/kg | R.A. (2) | mg/kg | R.A. (2) | |
| 8 | 0.055 | 0.91 | 5.23 | 0.14 | 95.09 |
| 9 | 0.063 | 0.79 | 3.98 | 0.18 | 63.17 |
| 11 | 0.077 | 0.65 | 6.09 | 0.12 | 79.09 |
| 12 | 0.022 | 2.27 | 0.75 | 0.98 | 34.09 |
| 14 | 0.042 | 1.19 | 1.0 | 0.73 | 23.81 |
| 16 | 0.046 | 1.09 | 1.33 | 0.55 | 28.91 |
| 17 | 0.046 | 1.09 | 2.76 | 0.27 | 60.00 |
| 30 | 0.034 | 1.47 | 4.1 | 0.18 | 120.59 |
| 58 | 0.10 | 0.50 | 5.62 | 0.13 | 56.20 |
| 65 | 0.53 | 0.09 | >31.6 | <0.02 | >59.62 |
| Amezinium | 0.05 | 1.00 | 0.733 | 1.00 | 14.66 |
| German Laid-Open Application DOS 2,245,248 Example 1 | 0.018 | 2.78 | 0.40 | 1.83 | 22.22 |

(1) Dose which increases the blood pressure of the pithed rat by 20%
(2) Relative activity: amezinium = 1.00
(3) Dose which inhibits the reserpine-induced hypothermia of the mouse by 50%
(4) $Q = \dfrac{\text{ED 50\%, reserpine antagonism}}{\text{ED 20\%, hypertensive action}}$ From the Table, it can be seen that particularly preferred compounds of the formula (I) are those in which $R^1$ is —CO—$R^3$ where $R^3$ is alkyl of 1 to 7 carbon atoms, benzyl, unsubstituted or methyl-substituted cycloalkyl of 3 to 6 ring carbon atoms, alkenyl of 3 carbon atoms, or phenyl which is unsubstituted or monosubstituted or disubstituted by fluorine, chlorine, methyl, methoxy or trifluoromethyl, or $R^1$ is —CO—Y—$R^4$ where Y is oxygen and $R^4$ is alkyl of 1 to 4 carbon atoms, benzyl, phenyl or alkenyl of 3 carbon atoms, or $R^1$ is

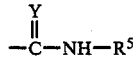

where Y is sulfur when $R^5$ is alkyl of 1 to 3 carbon atoms, or Y is oxygen when $R^5$ is alkyl of 1 to 4 carbon atoms, benzyl, or phenyl which is unsubstituted or monosubstituted by fluorine, chlorine, methyl, methoxy or trifluoromethyl, and $R^2$ is hydrogen, methoxy or ethoxy, and their addition salts with physiologically tolerated acids.

Accordingly, the present invention also relates to therapeutic agents or formulations which in addition to conventional carriers and diluents contain a compound of the formula I, or a physiologically tolerated addition salt thereof with an acid, as the active compound, and to the use of the novel compounds for therapeutic purposes.

The therapeutic agents or formulations are prepared in a conventional manner using an appropriate dose with the conventional carriers or diluents and the conventional pharmaceutical auxiliaries, in accordance with the desired route of administration (cf. R. Voigt, Lehrbuch der pharmazeutischen Technologie, VEB Verlag Volk und Gesundheit, Berlin 1975). A suitable individual therapeutic dose is from 1 to 500 mg, preferably from 5 to 100 mg.

The preferred formulations are those suitable for oral administration. Examples of these are tablets, film tablets, coated tablets, capsules, pills, powders, solutions, suspensions and depot forms.

Of course, formulations for parenteral administration, eg. injection solutions, are also suitable. Suppositories are a further example of suitable formulations.

For practical use, the compounds to be employed according to the invention are formulated with the carriers conventionally used in pharmaceutical production. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, disintegrating agents, eg. corn starch, alginic acid or polyvinylpyrrolidone, binders, eg. starch or gelatin, lubricants, eg. magnesium stearate or talc, and/or agents for achieving a depot effect, eg. carboxypolymethylene, carboxymethylcellulose, cellulose acetate phthalate or polyvinylacetate. The tablets can also consist of a plurality of layers.

Accordingly, coated tablets may be prepared by coating cores, prepared similarly to the tablets, with agents conventionally used in tablet coatings, for example polyvinylpyrrolidone or shellac, gum arabic, talc, titanium dioxide or sugar. The coating can also consist of a plurality of layers, and the auxiliaries mentioned above in connection with tablets may be used therein.

Solutions or suspensions containing the novel active compounds may additionally contain flavor improvers, such as saccharin, a cyclamate or sugar, and, for example, flavorings, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules.

Suitable suppositories can be prepared, for example, by mixing the active compounds with appropriate carriers, such as neutral fats or polyethylene glycol or their derivatives.

The Examples which follow illustrate the invention.

EXAMPLE 1

15.0 g (72.2 millimoles) of 1,4-dihydro-4-imino-1-phenylpyridazine hydrochloride in 100 ml of acetic anhydride were heated at 100° C. for 2 hours, while stirring. The mixture was cooled and then filtered under suction, and the residue was washed with acetone and recrystallized from ethanol. 13.3 g (74% of theory) of 4-acetylimino-1,4-dihydro-1-phenylpyridazine hydrochloride were isolated as colorless crystals of melting point 257°–260° C.

Analysis for $C_{12}H_{12}ClN_3O$ (249.7): Calculated: C 57.7, H 4.8, Cl 14.2, N 16.8%. Found: C 57.8, H 5.0, Cl 13.9, N 16.8%.

EXAMPLE 2

2 drops of concentrated sulfuric acid were added to 8.0 g (29.4 millimoles) of 1,4-dihydro-4-imino-1-phenylpyridazine perchlorate in 100 ml of acetic anhydride, and the mixture was refluxed for a short time, cooled and then filtered under suction. 7.0 g (76% of theory) of 4-acetylimino-1,4-dihydro-1-phenylpyridazine perchlorate remained as the residue, giving a product of melting point 229°–231° C. (decomposition on recrystallization from acetonitrile).

Analysis for $C_{12}H_{12}ClN_3O_5$ (313.7): Calculated: C 45.9, H 3.9, Cl 11.3, N 13.4%. Found: C 46.1, H 3.8, Cl 11.7, N 13.7%.

EXAMPLE 3

5.0 g (24.1 millimoles) of 1,4-dihydro-4-imino-1-phenylpyridazine hydrochloride in 50 ml of propionyl chloride were refluxed for 20 hours, while stirring. The mixture was cooled and then filtered under suction, and the residue was recrystallized from ethanol/methyl tert.-butyl ether. 2.6 g (41% of theory) of 1,4-dihydro-1-phenyl-4-(propionylimino)-pyridazine hydrochloride were isolated as slightly yellowish crystals of melting point 214°–215° C.

Analysis for $C_{13}H_{14}ClN_3O$ (263.7): Calculated: C 59.2, H 5.4, Cl 13.4, N 15.9%. Found: C 59.1, H 5.3, Cl 13.3, N 15.8%.

EXAMPLE 4

5.0 g (24.1 millimoles) of 1,4-dihydro-4-imino-1-phenylpyridazine hydrochloride in 50 ml of butyryl chloride were refluxed for 15 hours, while stirring. The mixture was cooled and then filtered under suction, and the residue was washed with acetone and recrystallized from isopropanol. 4.8 g (72% of theory) of 4-butyrylimino-1,4-dihydro-1-phenylpyridazine hydrochloride were isolated as pale beige crystals of melting point 205°–208° C.

Analysis for $C_{14}H_{16}ClN_3O$ (277.8):

Calculated: C 60.5, H 5.8, Cl 12.8, N 15.1%. Found: C 60.4, H 5.8, Cl 13.0, N 15.2%.

EXAMPLE 5

5.0 g (21.4 millimoles) of 1,4-dihydro-4-imino-1-phenylpyridazine hydrochloride in 20 ml of isobutyryl chloride were refluxed for 20 hours, while stirring. The mixture was cooled and then filtered under suction, and the residue was washed with acetone and recrystallized from ethanol/methyl tert.-butyl ether. 4.5 g (67% of theory) of 1,4-dihydro-4-isobutyrylimino-1-phenylpyridazine hydrochloride were isolated as colorless crystals of melting point 240°–242° C.

Analysis for $C_{14}H_{16}ClN_3O$ (277.8): Calculated: C 60.5, H 5.8, Cl 12.8, N 15.1% Found: C 60.6, H 5.9, Cl 13.0, H 15.2%

EXAMPLE 6

11.5 g (114 millimoles) of triethylamine were added dropwise to 9.3 g (44.8 millimoles) of 1,4-dihydro-4-imino-1-phenylpyridazine hydrochloride and 5.3 g (49.7 millimoles) of isobutyryl chloride in 50 ml of methylene chloride at room temperature, while stirring. After the addition was complete, stirring was continued for 4 hours at room temperature, after which water was added to the reaction mixture. The organic phase was separated off and mixed thoroughly with dilute hydrochloric acid (100 ml of water and 20 ml of concentrated hydrochloric acid). The methylene chloride phase was discarded, and the aqueous layer was brought to pH 10 with sodium hydroxide solution. The resulting solid substance was filtered off under suction, washed with water, dried and recrystallized from toluene/hexane. 5.1 g (47% of theory) of 1,4-dihydro-4-isobutyrylimino-1-phenylpyridazine were isolated as yellowish beige crystals of melting point 138° C.

Analysis for $C_{14}H_{15}N_3O$ (241.3): Calculated: C 69.7, H 6.3, N 17.4%. Found: C 69.6, H 6.2, N 17.7%.

EXAMPLE 7

6.0 g (28.9 millimoles) of 1,4-dihydro-4-imino-1-phenylpyridazine hydrochloride in 40 ml of valeryl chloride were kept at 120° C. for 20 hours, while stirring. The mixture was cooled and then filtered under suction, and the residue was washed with acetone and recrystallized first from ethanol/methyl tert.-butyl ether and then from ethanol/acetone. 3.4 g (40% of theory) of 1,4-dihydro-1-phenyl-4-(valerylimino)-pyridazine hydrochloride were isolated as pale yellowish crystals of melting point 180°–182° C.

Analysis for $C_{15}H_{18}ClN_3O$ (291.8): Calculated: C 61.7, H 6.2, Cl 12.2, N 14.4%. Found: C 61.8, H 6.2, Cl 11.9, N 14.5%.

EXAMPLE 8

When the procedure described in Example 7 was carried out using octanoyl chloride instead of valeryl chloride, 2.9 g (30% of theory) of 1,4-dihydro-4-octanoylimino-1-phenylpyridazine hydrochloride were isolated as colorless crystals of melting point 167°–169° C., after recrystallization from ethanol/methyl tert.-butyl ether.

Analysis for $C_{18}H_{24}ClN_3O$ (333.9): Calculated: C 64.8, H 7.2, Cl 10.6, N 12.6%. Found: C 64.9, H 7.2, Cl 11.0, N 12.6%.

EXAMPLE 9

6.0 g (28.9 millimoles) of 1,4-dihydro-4-imino-1-phenylpyridazine hydrochloride in 50 ml of phenylacetyl chloride were kept at 120° C. for 6 hours, while stirring. The mixture was cooled and then evaporated down, and the residue was treated with methanol/methyl tert.-butyl ether. The solid was filtered off under suction and recrystallized first from ethanol and then from ethanol/acetone with the addition of active charcoal. 3.9 g (41% of theory) of 1,4-dihydro-1-phenyl-4-[(phenylacetyl)-imino]-pyridazine hydrochloride were isolated as pale beige crystals of melting point 208°–210° C.

Analysis for $C_{18}H_{16}ClN_3O$ (325.8): Calculated: C 66.4, H 5.0, Cl 10.9, N 12.9%. Found: C 66.5, H 5.0, Cl 11.2, N 13.0%.

EXAMPLE 10

6.0 g (28.9 millimoles) of 1,4-dihydro-4-imino-1-phenylpyridazine hydrochloride in 35 ml of cyclopropanecarboxylic acid chloride were refluxed for 20 hours, while stirring. The mixture was cooled and then filtered under suction, and the residue was washed with acetone and recrystallized from isopropanol. 5.1 g (64% of theory) of 4-(cyclopropylcarbonyl)-imino-1,4-dihydro-1-phenylpyridazine hydrochloride were isolated as pale beige crystals of melting point 245°–247° C.

Analysis for $C_{14}H_{14}ClN_3O$ (275.7): Calculated: C 61.0, H 5.1, Cl 12.9, N 15.2%. Found: C 61.0, H 5.2, Cl 13.2, N 15.0%.

EXAMPLE 11

6.0 g (28.9 millimoles) of 1,4-dihydro-4-imino-1-phenylpyridazine hydrochloride and 15 ml of cyclobutanecarboxylic acid chloride in 10 ml of toluene were refluxed for 16 hours, while stirring. The mixture was cooled and then filtered under suction, and the residue was washed with acetone and recrystallized from ethanol. 4.2 g (50% of theory) of 4-(cyclobutylcarbonyl)-imino-1,4-dihydro-1-phenylpyridazine hydrochloride were isolated as colorless crystals of melting point 232°–235° C.

Analysis for $C_{15}H_{16}ClN_3O$ (289.8): Calculated: C 62.2, H 5.6, Cl 12.2, N 14.5%. Found: C 62.4, H 5.5, Cl 12.2, N 14.5%.

EXAMPLE 12

24.0 g (237 millimoles) of triethylamine were added dropwise to 15.0 g (72.2 millimoles) of 1,4-dihydro-4-imino-1-phenylpyridazine hydrochloricde and 12.8 g (~98 millimols) of ~80% strength methacryloyl chloride in 200 ml of methylene chloride at room temperature, while stirring. After the addition was complete, stirring was continued for a further 2 hours at room temperature, after which water was added to the reaction mixture. The organic phase was separated off, washed with water and evaporated down. The residue was recrystallized three times from toluene. 3.6 g (21% of theory) of 1,4-dihydro-4-methacryloylimino-1-phenylpyridazine were isolated as yellow crystals of melting point 136° C.

Analysis for $C_{14}H_{13}N_3O$ (239.3): Calculated: C 70.3, H 5.5, N 17.6%. Found: C 70.4, H 5.5, N 17.6%.

EXAMPLE 13

6.0 (28.9 millimoles) of 1,4-dihydro-4-imino-1-phenylpyridazine hydrochloride in 50 ml of benzoyl chloride were kept at 120° C. for 10 hours, while stirring. The mixture was cooled and then filtered under suction, and the residue was washed with acetone and recrystallized from isopropanol. 3.3 g (37% of theory) of 4-benzoylimino-1,4-dihydro-1-phenylpyridazine hydrochloride were isolated as pale beige crystals of melting point 225°–226° C. (decomposition).

Analysis for $C_{17}H_{14}ClN_3O$ (311.8): Calculated: C 65.5, H 4.5, Cl 11.4, N 13.5%. Found: C 65.6, H 4.5, Cl 11.0, N 13.5%.

EXAMPLE 14

10.0 g (48.2 millimoles) of 1,4-dihydro-4-imino-1-phenylpyridazine hydrochloride and 20 ml (26.8 g, 169 millimoles) of 4-fluorobenzoyl chloride in 30 ml of toluene were kept at 120° C. for 5 hours, while stirring. The mixture was cooled and the product was then filtered off under suction and recrystallized from ethanol. 6.2 g (39% of theory) of 1,4-dihydro-4-(4-fluorobenzoyl)-imino-1-phenylpyridazine hydrochloride were isolated as pale beige crystals of melting point 257°–258° C.

Analysis for $C_{17}H_{13}ClFN_3O$ (329.8):
Calculated: C 61.9, H 4.0, Cl 10.8, F 5.8, N 12.7%.
Found: C 62.0, H 4.0, Cl 10.8, F 5.9, N 12.9%.

EXAMPLE 15

9.6 g (94.9 millimoles) of triethylamine were added dropwise to 7.5 g (36.1 millimoles) of 1,4-dihydro-4-imino-1-phenylpyridazine hydrochloride and 8.3 g (39.6 millimoles) of 3,5-dichlorobenzoyl chloride in 100 ml of methylene chloride at room temperature, while stirring.

Stirring was continued at room temperature for a further 2 hours, after which the product ws filtered off under suction, washed first with water and then with acetone and recrystallized from toluene. 8.0 g (64% of theory) of 4-(3,5-dichlorobenzoyl)-imino-1,4-dihydro-1-phenylpyridazine were isolated as yellow crystals of melting point 242°–244° C.

Analysis for $C_{17}H_{11}Cl_2N_3O$ (344.2): Calculated: C 59.3, H 3.2, Cl 20.6, N 12.2%. Found: C 59.5, H 3.3, Cl 20.7, N 12.3%.

EXAMPLE 16

80 ml of toluene were added to a solution of 10.0 g (48.2 millimoles) of 1,4-dihydro-4-imino-1-phenylpyridazine hydrochloride in 80 ml of water. First 6.8 g (48.4 millimoles) of benzoyl chloride and then, in the course of 15 minutes, 4.0 g (100 millimoles) of NaOH in 20 ml of water were added to the two-phase system at room temperature, whilst stirring, the mixture was stirred for a further hour at room temperature and the product was then filtered off under suction. The solid obtained was washed with water, dried and recrystallized from ethanol. 9.5 g (72% of theory) of 4-benzoylimino-1,4-dihydro-1-phenylpyridazine were isolated as yellow crystals of melting point 175°–176° C.

Analysis for $C_{17}H_{13}N_3O$ (275.3): Calculated: C 74.2, H 4.8, N 15.3, O 5.8%. Found: C 74.0, H 4.8, N 15.4, O 5.9%.

Examples 17 to 28 are summarized in Table 3 below. These pyridazinone-imines are prepared by the method described in Example 16.

TABLE 3

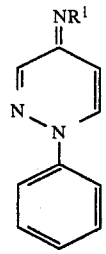

| Example | $R^1$ | Melting point [°C.] | Yield (%) | | C | H | Cl | N | O |
|---|---|---|---|---|---|---|---|---|---|
| 17 | -CO-C₆H₄-Cl (o) | 136–138 (ethanol/toluene) | 60 | calc. | 65.9 | 3.9 | 11.4 | 13.6 | 5.2 |
| | | | | found | 65.6 | 4.1 | 12.1 | 13.5 | 5.1 |
| 18 | -CO-C₆H₄-Cl (m) | 212–214 (toluene) | 61 | calc. | 65.9 | 3.9 | 11.4 | 13.6 | 5.2 |
| | | | | found | 65.9 | 3.9 | 11.3 | 13.7 | 5.2 |
| 19 | -CO-C₆H₄-Cl (p) | 216 (toluene) | 68 | calc. | 65.9 | 3.9 | 11.4 | 13.6 | 5.2 |
| | | | | found | 65.9 | 4.0 | 11.6 | 13.6 | 5.2 |
| 20 | -CO-C₆H₃-2,4-Cl₂ | 159–160 (toluene) | 50 | calc. | 59.3 | 3.2 | 20.6 | 12.2 | |
| | | | | found | 59.6 | 3.2 | 20.7 | 12.5 | |
| 21 | -CO-C₆H₃-2,6-Cl₂ | 163–165 (toluene) | 27 | calc. | 59.3 | 3.2 | 20.6 | 12.2 | 4.6 |
| | | | | found | 59.4 | 3.3 | 20.5 | 12.3 | 4.6 |

| | | | | | C | H | Cl/(F) | N | O |
|---|---|---|---|---|---|---|---|---|---|
| 22 | -CO-C₆H₃-3,4-Cl₂ | 159–160 (toluene) | 40 | calc. | 59.3 | 3.2 | 20.6 | 12.2 | 4.6 |
| | | | | found | 59.5 | 3.3 | 20.4 | 12.2 | 4.8 |

TABLE 3-continued

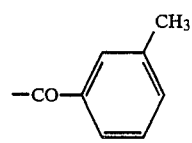

| Example | R¹ | Melting point [°C.] | Yield (%) | Analysis (%) | | | |
|---|---|---|---|---|---|---|---|
| 23 | 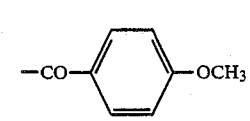 | 158–159 (toluene) | 54 | calc.<br>found | 74.7<br>74.8 | 5.2<br>5.3 | —<br>— | 14.5<br>14.7 |
| 24 | 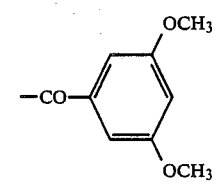 | 153–154 (toluene) | 85 | calc.<br>found | 70.8<br>70.8 | 5.0<br>5.0 | —<br>— | 13.8<br>13.9 |
| 25 | 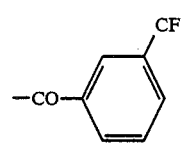 | 155 (toluene) | 38 | calc.<br>found | 68.0<br>68.3 | 5.1<br>5.1 | —<br>— | 12.5<br>12.7 |
| 26 | 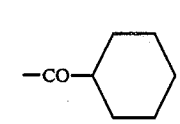 | 163 (isobutanol) | 65 | calc.<br>found | 63.0<br>63.0 | 3.5<br>3.6 | (16.6)<br>(16.9) | 12.2<br>12.5 |
| 27 | —CO—⬡ | 159 (toluene/cyclohexane) | 46 | calc.<br>found | 72.6<br>72.5 | 6.8<br>6.8 | —<br>— | 14.9<br>15.0 |
| 28 | 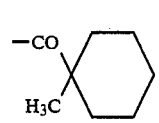 | 158 (toluene/cyclohexane) | 39 | calc.<br>found | 73.2<br>73.3 | 7.2<br>7.1 | —<br>— | 14.2<br>14.2 |

EXAMPLE 29

6.0 g (28.9 millimoles) of 1,4-dihydro-4-imino-1-phenylpyridazine hydrochloride in 45 ml of ethyl chloroformate were refluxed for 4 days, while stirring. The mixture was cooled and then filtered under suction, and the residue was chromatographed over an $SiO_2$ column (chloroform/methanol/formic acid (90:9.5:0.5 vol. %). The eluted 1,4-dihydro-4-(ethoxycarbonyl)-imino-1-phenylpyridazine hydrochloride was recrystallized from methanol/ether. 2.3 g (28% of theory) of slightly reddish crystals of melting point 161°–162° C. (decomposition) were isolated.

Analysis for $C_{13}H_{14}ClN_3O_2$ (279.7): Calculated: C 55.8, H 5.0, Cl 12.7, N 15.0%. Found: C 55.8, H 5.1, Cl 12.6, N 15.1%.

EXAMPLE 30

6.0 g (28.9 millimoles) of 1,4-dihydro-4-imino-1-phenylpyridazine hydrochloride in 40 ml of phenyl chloroformate were kept at 95° C. for 4 days, while stirring. The mixture was cooled and then filtered under suction, and the residue was recrystallized first from ethanol/methyl tert.-butyl ether and then from dimethylformamide/ethyl acetate. 3.3 g (35% of theory) of 1,4-dihydro-4-(phenoxycarbonyl)-imino-1-phenylpyridazine hydrochloride were isolated as pale orange crystals of melting point 222°–223° C.

Analysis for $C_{17}H_{14}ClN_3O_2$ (327.8): Calculated: C 62.3, H 4.3, Cl 10.8, N 12.8%. Found: C 62.3, H 4.4, Cl 10.9, N 13.1%.

EXAMPLE 31

5.3 g (52.4 millimoles) of triethylamine were added dropwise to 10.0 g (48.2 millimoles) of 1,4-dihydro-4-imino-1-phenylpyridazine hydrochloride in 25 ml (24.2 g 424 millimoles) of methyl isocyanate at room temperature, while stirring. After the addition was complete, the reaction mixture was diluted with 50 ml of acetone, and stirred for a further 2 hours at room temperature. The product was filtered off under suction, washed with water and acetone, and recrystallized from methanol. 3.0 g (27% of theory) of 1,4-dihydro-4-(methylcarbamyl)-imino-1-phenylpyridazine were isolated as slightly greenish crystals of melting point 205°–206° C.

Analysis for $C_{12}H_{12}N_4O$ (228.3): Calculated: C 63.1, H 5.3, N 24.5%. Found: C 63.1, H 5.2, N 24.7%.

EXAMPLE 32

5.3 g (52.4 millimoles) of triethylamine were added dropwise to 10.0 g (48.2 millimoles) of 1,4-dihydro-4-imino-1-phenylpyridazine hydrochloride in 20 ml (22.6 g, 167 millimoles) of phenyl isothiocyanate at room temperature, while stirring. After the addition was complete, the reaction mixture was stirred for a further 2 hours at room temperature and then diluted with 30 ml of acetone. The product was filtered off under suction, washed with acetone, with water and again with acetone, and recrystallized from ethanol. 6.0 g (41% of theory) of 1,4-dihydro-1-phenyl-4-[(phenylthiocarbamyl)-imino]-pyridazine were isolated as orange crystals of melting point 171°–173° C.

Analysis for $C_{17}H_{14}N_4S$ (306.4): Calculated: C 66.6, H 4.6, N 18.3, S 10.5%. Found: C 66.7, H 4.6, N 18.4, S 10.3%.

Examples 33 to 46 are summarized in Table 4 below. These pyridazinone-imines were prepared by the method described in Example 16. Instead of the benzoyl chloride used in that Example, a chloroformate (Examples 33 to 35), S-ethyl chlorothioformate (Example 36), an isocyanate (Examples 37 to 44) or an isothiocyanate (Examples 45 and 46) was employed. When an isocyanate or isothiocyanate was employed, only 50 millimols of NaOH were used per 48.2 millimoles of substrate.

TABLE 4

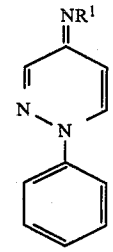

| Example | R¹ | Melting point [°C.] | Yield (%) | Analysis (%) | | | | |
|---|---|---|---|---|---|---|---|---|
| | | | | | C | H | N | S |
| 33 | —CO—O—(CH₂)₃—CH₃ | 118–119 (toluene/cyclohexane) | 32 | calc. | 66.4 | 6.3 | 15.5 | — |
| | | | | found | 66.8 | 6.3 | 15.5 | — |
| 34 | —CO—O—CH₂—C₆H₅ | 115 (dimethylformamide/water) | 24 | calc. | 70.8 | 5.0 | 13.8 | — |
| | | | | found | 70.7 | 5.0 | 13.7 | — |
| 35 | —CO—O—CH₂—CH=CH₂ | 123 (toluene) | 61 | calc. | 65.9 | 5.1 | 16.5 | — |
| | | | | found | 66.1 | 5.1 | 16.5 | — |
| 36 | —CO—S—CH₂—CH₃ | 120–121 (toluene) | 26 | calc. | 60.2 | 5.1 | 16.2 | 12.4 |
| | | | | found | 60.1 | 5.0 | 16.3 | 12.2 |
| 37 | —CO—NH—CH(CH₃)₂ | 137–138 (methanol) | 31 | calc. | 65.6 | 6.3 | 21.9 | — |
| | | | | found | 65.4 | 6.4 | 22.0 | — |
| 38 | —CO—NH—(CH₂)₃—CH₃ | 142–143 (toluene) | 61 | calc. | 66.6 | 6.7 | — | 20.7 |
| | | | | found | 66.7 | 6.6 | — | 20.7 |
| 39 | —CO—NH—CH₂—C₆H₅ | 177 (ethanol) | 71 | calc. | 71.0 | 5.3 | — | 18.4 |
| | | | | found | 71.0 | 5.4 | — | 18.6 |
| | | | | | C | H | Cl | N |
| 40 | —CO—NH—C₆H₅ | 164 (toluene) | 50 | calc. | 70.3 | 4.9 | — | 19.3 |
| | | | | found | 70.5 | 4.9 | — | 19.3 |
| 41 | —CO—NH—C₆H₄—CH₃ (o-tolyl) | 129–131 (toluene) | 42 | calc. | 71.0 | 5.3 | — | 18.4 |
| | | | | found | 71.0 | 5.3 | — | 18.7 |

TABLE 4-continued

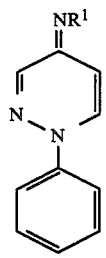

| Example | R$^1$ | Melting point [°C.] | Yield (%) | Analysis (%) | | | | |
|---|---|---|---|---|---|---|---|---|
| 42 | —CO—NH—⟨⟩—OCH$_3$ | 150–151 (toluene) | 43 | calc. found | 67.5 67.6 | 5.0 5.0 | — — | 17.5 17.6 |
| 43 | —CO—NH—⟨⟩—Cl | 152–153 (ethanol) | 62 | calc. found | 62.9 62.9 | 4.0 3.9 | 10.9 11.0 | 17.3 17.4 |

| | | | | | C | H | Cl/(F) | N | S |
|---|---|---|---|---|---|---|---|---|---|
| 44 | —CO—NH—⟨⟩—CF$_3$ | 167 (butanol) | 36 | calc. found | 60.3 60.5 | 3.7 3.7 | (15.9) (15.6) | 15.6 15.7 | — — |
| 45 | —CS—NH—CH$_2$—⟨⟩ | 142–143 (methylene chloride/hexane) | 58 | calc. found | 67.5 67.4 | 5.0 5.1 | — — | 17.5 17.6 | 10.0 9.8 |
| 46 | —CS—NH—⟨⟩—Cl | 156–159 (ethanol) | 42 | calc. found | 59.9 59.9 | 3.8 4.1 | 10.4 10.7 | 16.4 16.2 | 9.4 9.4 |

EXAMPLE 47

10.0 g (48.2 millimoles) of 1,4-dihydro-4-imino-1-phenylpyridazine hydrochloride and 10 ml (12.2 g, 89.5 millimoles) of ethoxyoxalyl chloride in 50 ml of toluene were refluxed for 4 hours, while stirring. The mixture was cooled and then filtered under suction, and the residue was washed with acetone and recrystallized from ethanol. 6.5 g (44% of theory) of 1,4-dihydro-4-(ethoxyoxalyl)-imino-1-phenylpyridazine hydrochloride were isolated as slightly yellowish crystals of melting point 169°–170° C.

Analysis for C$_{14}$H$_{14}$ClN$_3$O$_3$ (307.7): Calculated: C 54.6, H 4.6, Cl 11.5, N 13.7%. Found: C 54.6, H 4.5, Cl 11.5, N 13.6%.

EXAMPLE 48

A few drops of concentrated sulfuric acid were added to 15.5 g (49.5 millimoles) of 1,4-dihydro-4-imino-6-methoxy-1-phenylpyridazine methyl-sulfate in 100 ml of acetic anhydride, and the mixture was then heated at 85° C., while stirring, until a clear solution formed. Thereafter, the solution was evaporated down under reduced pressure, the residue was dissolved in about 100 ml of water and 10 g of 70% strength perchloric acid were added to the solution. The precipitate which formed was filtered off under suction and dried under reduced pressure. 15.0 g (88% of theory) of 4-acetylimino-1,4-dihydro-6-methoxy-1-phenylpyridazine perchlorate of melting point 205°–207° C. (decompositon) were isolated.

Analysis for C$_{13}$H$_{14}$ClN$_3$O$_6$ (343.7): calculated: C 45.4 H 4.1, Cl 10.3, N 12.2%. Found: C 46.4, H 4.4, Cl 10.3, N 12.4%.

Examples 49 to 57 are summarized in Table 5 below. These compounds were prepared by the method described in Example 48. For Examples 49, 51, 53, 55 and 57, 1,4-dihydro-4-imino-6-methoxy-1-phenylpyridazine methyl-sulfate was replaced by 1,4-dihydro-6-ethoxy-4-imino-1-phenylpyridazine ethyl-sulfate as the substrate.

TABLE 5

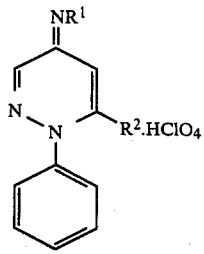

| Example | R¹ | R² | Melting Point [°C.] | Yield (%) | | Analysis (%) | | | |
|---|---|---|---|---|---|---|---|---|---|
| | | | | | | C | H | Cl | N |
| 49 | —CO—CH₃ | —OC₂H₅ | 131–136 | 66 | calc. | 47.0 | 4.5 | 9.9 | 11.7 |
| | | | | | found | 46.8 | 4.5 | 10.1 | 11.8 |
| 50 | —CO—CH₂—CH₃ | —OCH₃ | 130–140 | 49 | calc. | 47.0 | 4.5 | 9.9 | 11.7 |
| | | | | | found | 47.1 | 4.6 | 9.4 | 11.8 |
| 51 | —CO—CH₂—CH₃ | —OC₂H₅ | 173–174 | 60 | calc. | 48.5 | 4.9 | 9.5 | 11.3 |
| | | | | | found | 48.5 | 4.9 | 9.5 | 11.5 |
| 52 | —CO—(CH₂)₂—CH₃ | —OCH₃ | 141–142 | 33 | calc. | 48.5 | 4.9 | 9.5 | 11.3 |
| | | | | | found | 48.6 | 5.0 | 9.5 | 11.3 |
| 53 | —CO—(CH₂)₂—CH₃ | —OC₂H₅ | 209–211 | 52 | calc. | 49.8 | 5.2 | 9.2 | 10.9 |
| | | | | | found | 50.1 | 5.4 | 9.1 | 11.2 |
| 54 | —CO—(CH₂)₄—CH₃ | —OCH₃ | 149–150 | 20 | calc. | 51.1 | 5.5 | 8.9 | 10.5 |
| | | | | | found | 51.1 | 5.6 | 9.2 | 10.5 |
| 55 | —CO—(CH₂)₄—CH₃ | —OC₂H₅ | 117–121 | 22 | calc. | 52.2 | 5.9 | 8.6 | 10.2 |
| | | | | | found | 52.4 | 5.9 | 8.5 | 10.0 |
| 56 | —CO—(CH₂)₅—CH₃ | —OCH₃ | 152–153 | 27 | calc. | 52.2 | 5.9 | 8.6 | 10.2 |
| | | | | | found | 52.4 | 5.9 | 8.8 | 10.1 |
| 57 | —CO—(CH₂)₅—CH₃ | —OC₂H₅ | 73–74 | 49 | calc. | 53.3 | 6.1 | 8.3 | 9.8 |
| | | | | | found | 53.7 | 6.2 | 8.4 | 9.7 |

EXAMPLE 58

100 ml of toluene were added to a solution of 15.0 g (47.9 millimoles) of 1,4-dihydro-4-imino-6-methoxy-1-phenylpyridazine methyl-sulfate in 200 ml of water, the solution having been prepared by heating the components. First 7.8 g (49.8 millimoles) of phenyl chloroformate and thereafter, in the course of 30 minutes, a solution of 4.0 g (100 millimoles) of sodium hydroxide in 35 ml of water were added to the two-phase system at room temperature, while stirring. Stirring was continued for 10 minutes at room temperature, after which the phases were separated, the reddish toluene phase was dried and concentrated, and the residue was recrystallized from toluene with the addition of animal charcoal. 6.5 g (42% of theory) of 1,4-dihydro-6-methoxy-4-(phenoxycarbonyl)-imino-1-phenylpyridazine of melting point 114° C. were isolated.

Analysis for C₁₈H₁₅N₃O₃ (321.3): calculated: C 67.3, H 4.7, N 13.1%. Found: C 67.2, H 4.9, N 13.1%.

Examples 59 to 83 are summarized in Table 6 below. These pyridazinone-imines were prepared by the method described in Example 58, except that in Examples 61, 63, 65, 67, 70 and 75, 1,4-dihydro-4-imino-6-methoxy-1-phenylpyridazine methyl-sulfate was replaced by 1,4-dihydro-6-ethoxy-4-imino-1-phenylpyridazine ethyl-sulfate as the substrate. Furthermore, only in Examples 69 to 72 was the reagent used a chloroformate, as in Example 58. In the other Examples, a carboxylic acid chloride (Examples 59 to 68 and 76 to 80), S-ethyl chlorothioformate (Example 73) or an isocyanate (Examples 74, 75, 81, 82 and 83) was used as the reagent.

When an isocyanate was employed, only 50 millimoles of sodium hydroxide were used per 47.9 millimoles of substrate. In the case of Examples 62 to 68, 72 to 74 and 78 to 83, sodium hydroxide solution was added, the mixture was stirred further at room temperature and the product was then filtered off under suction. The solid obtained was washed with water, dried and recrystallized.

TABLE 6

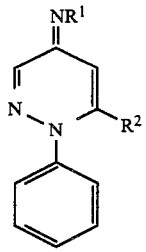

| Example | R¹ | R² | Melting Point [°C.] | Yield (%) | | C | H | Cl | F | N | S |
|---|---|---|---|---|---|---|---|---|---|---|---|
| | | | | | | | | Analysis (%) | | | |
| 59 | —CO—CH₂—C₆H₅ | —OCH₃ | 128–129 (ethyl acetate) | 3 | calc. found | 71.5 71.4 | 5.4 5.4 | | | 13.2 13.3 | |
| 60 | —CO—C₆H₅ | —OCH₃ | 145–147 (acetonitrile) | 48 | calc. found | 70.6 71.2 | 5.3 5.1 | | | 13.7 13.7 | |
| 61 | —CO—C₆H₅ | —OC₂H₅ | 167 (ethanol) | 69 | calc. found | 71.5 71.4 | 5.4 5.5 | | | 13.2 13.4 | |
| 62 | —CO—(3,5-diOCH₃-C₆H₃) | —OCH₃ | 151 (acetonitrile) | 49 | calc. found | 65.7 65.5 | 5.2 5.2 | | | 11.5 11.7 | |
| 63 | —CO—(3,5-diOCH₃-C₆H₃) | —OC₂H₅ | 161 (acetonitrile) | 40 | calc. found | 66.5 66.3 | 5.6 5.4 | | | 11.1 11.2 | |
| 64 | —CO—(2-Cl-C₆H₄) | —OCH₃ | 162 (acetonitrile) | 35 | calc. found | 63.6 63.6 | 4.2 4.2 | 10.4 10.7 | | 12.4 12.4 | |
| 65 | —CO—(2-Cl-C₆H₄) | —OC₂H₅ | 134 (toluene) | 34 | calc. found | 64.5 64.8 | 4.6 4.8 | 10.1 10.1 | | 11.9 11.8 | |
| 66 | —CO—(4-Cl-C₆H₄) | —OCH₃ | 188 (acetonitrile) | 60 | calc. found | 63.6 63.6 | 4.2 4.2 | 10.4 10.5 | | 12.4 12.3 | |
| 67 | —CO—(4-Cl-C₆H₄) | —OC₂H₅ | 129 (acetonitrile) | 39 | calc. found | 64.5 63.9 | 4.6 4.9 | 10.1 10.3 | | 11.9 11.7 | |

TABLE 6-continued

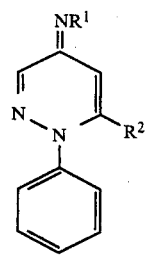

| Example | R¹ | R² | Melting Point [°C.] | Yield (%) | Analysis (%) | | | | | |
|---|---|---|---|---|---|---|---|---|---|---|
| | | | | | | C | H | Cl | F | N | S |
| 68 | -CO-C₆H₃(Cl)₂ (2,4-dichlorophenyl) | -OCH₃ | 166 (acetonitrile) | 43 | calc. found | 57.8 57.9 | 3.5 3.6 | 19.0 18.8 | | 11.2 11.2 | |
| 69 | CO—O—CH₂—CH₃ | —OCH₃ | 118 (naphtha) | 40 | calc. found | 61.5 61.6 | 5.5 5.5 | — — | | 15.4 15.5 | |
| 70 | —CO—O—CH₂—CH₃ | —OC₂H₅ | 70-72 (cyclohexane) | 45 | calc. found | 62.7 62.0 | 6.0 6.0 | | | 14.6 14.6 | — — |
| 71 | —CO—O—(CH₂)₃—CH₃ | —OCH₃ | 115 (toluene) | 47 | calc. found | 63.8 63.8 | 6.4 6.4 | | | 13.9 14.0 | — — |
| 72 | —CO—O—CH₂—CH=CH₂ | —OCH₃ | 115-120 (toluene) | 28 | calc. found | 63.2 62.7 | 5.2 5.3 | | | 14.7 14.4 | — — |
| 73 | —CO—S—CH₂—CH₃ | —OCH₃ | 122 (toluene) | 28 | calc. found | 58.1 58.2 | 5.1 5.3 | | | 14.5 14.8 | 11.1 10.8 |
| 74 | —CO—NH—CH₂—C₆H₅ | —OCH₃ | 110 (toluene) | 42 | calc. found | 68.3 67.5 | 5.4 5.5 | | | 16.8 16.8 | — — |
| 75 | —CO—NH—C₆H₅ | —OC₂H₅ | 154 (acetonitrile) | 24 | calc. found | 68.2 68.2 | 5.4 5.2 | | | 16.8 16.7 | — — |
| 76 | —CO—C₆H₄—OCH₃ | —OCH₃ | 156-158 | 21 | calc. found | 68.1 67.9 | 5.1 5.1 | — — | — — | 12.5 12.4 | |
| 77 | —CO—C₆H₄—CF₃ | —OCH₃ | 195-197 (ethanol) perchlorate | 44 | calc. found | 48.2 48.7 | 3.2 3.2 | 7.5 7.5 | 12.0 12.1 | 8.9 9.0 | |
| 78 | —CO—C₆H₄—CH₃ | —OCH₃ | 183-185 (acetonitrile) | 48 | calc. found | 71.5 71.3 | 5.4 5.3 | — — | — — | 13.2 13.3 | |
| 79 | —CO—C₆H₄—F | —OCH₃ | 175-176 (acetonitrile) | 32 | calc. found | 66.9 66.7 | 4.4 4.5 | — — | 5.9 5.9 | 13.0 13.2 | |
| 80 | —CO—C₆H₃(Cl)₂ (3,4-dichlorophenyl) | —OCH₃ | 188-190 (acetonitrile) | 65 | calc. found | 57.8 57.3 | 3.5 3.7 | 19.0 18.5 | — — | 11.2 11.2 | |

TABLE 6-continued

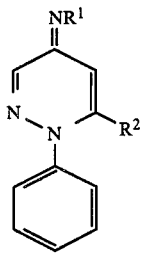

| Example | R¹ | R² | Melting Point [°C.] | Yield (%) | | Analysis (%) | | | | |
|---|---|---|---|---|---|---|---|---|---|---|
| | | | | | | C | H | Cl | F | N | S |
| 81 | —CO—NH—(3-Cl-phenyl) | —OCH₃ | 147–148 (acetonitrile) | 26 | calc. | 60.9 | 4.3 | 10.0 | — | 15.8 | |
| | | | | | found | 61.2 | 4.4 | 9.9 | — | 15.8 | |
| 82 | —CO—NH—phenyl | —OCH₃ | 137–138 (acetonitrile) | 17 | calc. | 67.5 | 5.0 | — | — | 17.5 | |
| | | | | | found | 67.5 | 5.1 | — | — | 17.5 | |
| 83 | —CO—NH—(4-F-phenyl) | —OCH₃ | 152–153 (acetonitrile) | 35 | calc. | 63.9 | 4.5 | — | 5.6 | 16.6 | |
| | | | | | found | 64.0 | 4.5 | — | 5.7 | 16.5 | |

EXAMPLE 84

70 ml of toluene were added to a solution of 7.5 g (36.1 millimoles) of 1,4-dihydro-4-imino-1-phenyl-pyridazine hydrochloride in 70 ml of water. First 2.6 g (36.6 millimols) of ethyl isocyanate and thereafter, in the course of 15 minutes, 1.5 g (37.5 millimols) of NaOH in 20 ml of water were added to the two-phase system at room temperature, while stirring. Stirring was continued for a further hour at room temperature, and the product was then filtered off under suction. The solid obtained was washed with water, dreid and recrystallized twice from methylene chloride/hexane. 4.0 g (46% of theory) of 1,4-dihydro-4-(ethylcarbamyl)-imino-1-phenylpyridazine were isolated as pale yellow crystals of melting point 142°–143° C.

Analysis for $C_{13}H_{13}N_4O$ (242.3): Calculated: C 64.4, H 5.8, N 23.1%. Found: C 64.3, H 5.9, N 23.3%.

EXAMPLE 85

When the procedure in Example 84 was followed using propyl isocyanate (3.1 g, 36.4 millimoles) instead of ethyl isocyanate, and the product was recrystallized from methylene chloride/hexane, 5.1 g (55% of theory) of 1,4-dihydro-1-phenyl-4-[(propylcarbamyl)-imino]-pyridazine were isolated as yellowish beige crystals of melting point 156°–157° C.

Analysis for $C_{14}H_{16}N_4O$ (256.3): Calculated: C 65.6, H 6.3, N 21.9%. Found: C 65.7, H 6.3, N 22.0%.

EXAMPLE 86

5.3 g (52.4 millimoles) of triethylamine were added dropwise to 10.0 g (48.2 millimoles) of 1,4-dihydro-4-imino-1-phenylpyridazine hydrochloride in 25 ml (26.7 g, 365 millimoles) of methyl isothiocyanate at room temperature, while stirring. After the addition was complete, the reaction mixture was diluted with 50 ml of acetone and stirred for a further 2 hours at room temperature. The product was filtered off under suction, washed with water and acetone and recrystallized from dimethylformamide/water. The crystals obtained were suspended in 25 ml of acetone, filtered off under suction, again suspended in 25 ml of acetone and filtered off under suction, and the product was recrystallized from isopropanol. 2.8 g (24% of theory) of 1,4-dihydro-4-(methylthiocarbamyl)-imino-1-phenylpyridazine were isolated as yellow crystals of melting point 177°–178° C. (decomposition).

Analysis for $C_{12}H_{12}N_4S$ (244.3): Calculated: C 59.0, H 5.0, N 22.9 S 13.1%. Found: C 59.2, H 4.9, N 23.0, S 12.8%.

EXAMPLE 87

5.3 g (52.4 millimoles) of triethylamine were added dropwise to 10.0 g (48.2 millimoles) of 1,4-dihydro-4-imino-1-phenylpyridazine hydrochloride in 25 ml (24.9 g, 285 millimoles) of ethyl isothiocyanate at room temperature, while stirring. After the addition was complete, the reaction mixture was diluted with 50 ml of acetone, stirred for a further 2 hours at room temperature and then filtered. The residue was discarded. The filtrate was evaporated down, and the solid which remained was recrystallized first from isopropanol and then from ethyl acetate/hexane. 1.0 g (8% of theory) of 1,4-dihydro-4-(ethylthiocarbamyl)-imino-1-phenylpyridazine was isolated as yellow crystals of melting point 134°–135° C.

Analysis for $C_{13}H_{14}N_4S$ (258.3): Calculated: C 60.4, H, 5.5, N 21.7, S 12.4%. Found: C 60.1, H 5.3, N 21.8, S 12.3%.

EXAMPLE 88

7.5 g (74.1 millimols) of triethylamine were added dropwise to 7.5 g (36.1 millimols) of 1,4-dihydro-4-imino-1-phenylpyridazine hydrochloride and 5.0 g (36.6 millimols) of ethoxyoxalyl chloride in 100 ml of methylene chloride at room temperature, while stirring. After the addition was complete, stirring was continued for a further 1 hour at room temperature, after which water was added to the reaction mixture. The organic phase was separated off, washed with water and evaporated down. The residue was recrystallized first from ethyl acetate and then from methylene chloride/petroleum ether. 3.9 g (40% of theory) of 1,4-dihydro-4-(ethoxyoxalyl)-imino-1-phenylpyridazine were isolated as yellow crystals of melting point 142°–143° C.

Analysis for $C_{14}H_{13}N_3O_3$ (271.3): Calculated: C 62.0, H 4.8, N 15.5%. Found: C 61.9, H 4.9, N 15.6%.

Formulation Examples prepared in a conventional manner:

| 1. Tablets: | |
|---|---|
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound is moistened with a 10% strength aqueous solution of polyvinylpyrrolidone and forced through a sieve of 1.0 mm mesh size, and the granules are dried at 50° C. They are then mixed with polyethylene glycol (mean molecular weight 4,000), hydroxypropylmethylcellulose, talc and magnesium stearate, and the mixture is pressed to give tablets weighing 240 mg.

| 2. Example of coated tablets: | |
|---|---|
| Active compound | 10 mg |
| Lactose | 90 mg |
| Corn starch | 60 mg |
| Polyvinylpyrrolidone | 6 mg |
| Magnesium stearate | 1 mg |
| | 167 mg |

The active compound, lactose and corn starch are mixed, moistened with an 8% strength aqueous solution of the polyvinylpyrrolidone, and granulated by passing throug a 1.5 mm mesh sieve. The granules are dreid at 50° C. and forced through a 1.0 mm sieve. The material thus obtained is mixed with magnesium stearate, and the mixture is pressed to form tablet cores. These are coated in a conventional manner with a shell consisting essentially of sugar and talc.

We claim:

1. A compound of the formula I

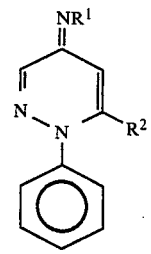

(I)

wherein
$R^1$ is

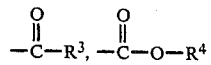

or

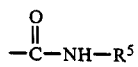

in which $R^3$ is alkyl of 1 to 3 carbon atoms, cyclopropyl or allyl, $R^4$ is alkyl of 1 to 3 carbon atoms or allyl and $R^5$ is alkyl of 1 to 3 carbon atoms, and $R_2$ is hydrogen, and its addition salts with a physiologically tolerated acid.

2. 1,4-Dihydro-1-phenyl-4-[(propylcarbamyl)-imino]-pyridazine, and its acid addition salts, as defined in claim 1.

3. 1,4-Dihydro-4-(methylcarbamyl)-imino-1-phenyl-pyridazine, and its acid addition salts, as defined in claim 1.

4. A compound of the formula I as defined in claim 1, wherein $R^1$ is —CO—$R^3$ and $R^3$ is $C_1$–$C_3$ alkyl or cyclopropyl and its addition salts with a physiologically tolerated salts.

5. A compound of the formula I as defined in claim 1, wherein $R^1$ is —CO—O—$R^4$ and $R^4$ is $C_1$–$C_3$-alkyl or allyl.

6. A compound of the formula I as defined in claim 1, wherein $R^1$ is

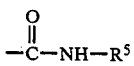

and $R^5$ is $C_1$–$C_3$-alkyl.

* * * * *